United States Patent
Bjornson et al.

(10) Patent No.: US 6,803,019 B1
(45) Date of Patent: Oct. 12, 2004

(54) LAMINATE MICROSTRUCTURE DEVICE AND METHOD FOR MAKING SAME

(75) Inventors: Torleif Ove Bjornson, Gilroy, CA (US); Laurence R. Shea, San Jose, CA (US)

(73) Assignee: Aclara Biosciences, Inc., Mountain View, CA (US)

(*) Notice: Subject to any disclaimer, the term of this patent is extended or adjusted under 35 U.S.C. 154(b) by 0 days.

(21) Appl. No.: 09/509,337

(22) PCT Filed: Oct. 15, 1998

(86) PCT No.: PCT/US98/21869
§ 371 (c)(1),
(2), (4) Date: Jun. 13, 2000

(87) PCT Pub. No.: WO99/19717
PCT Pub. Date: Apr. 22, 1999

Related U.S. Application Data

(63) Continuation-in-part of application No. 08/950,403, filed on Oct. 15, 1997.

(51) Int. Cl.[7] .............................................. G01N 27/00
(52) U.S. Cl. ........................ 422/66; 422/58; 422/82.01; 422/102
(58) Field of Search ...................... 422/58, 66, 82.01, 422/82.02, 100, 102

(56) References Cited

U.S. PATENT DOCUMENTS

| | | |
|---|---|---|
| 4,273,639 A | 6/1981 | Gottermeier ............ 204/195 R |
| 4,952,266 A | 8/1990 | Tsuruta et al. ............... 156/243 |
| 5,030,418 A | 7/1991 | Miyata ......................... 422/63 |
| 5,376,252 A * | 12/1994 | Ekstrom et al. |
| 5,411,858 A | 5/1995 | McGeehan et al. ............. 435/4 |
| 5,595,712 A | 1/1997 | Harbster et al. ............ 422/129 |
| 5,658,413 A | 8/1997 | Kaltenbach et al. ...... 156/272.8 |
| 5,880,071 A * | 3/1999 | Parce et al. .................. 204/453 |
| 5,885,470 A * | 3/1999 | Parce et al. .................... 216/33 |
| 6,375,871 B1 | 4/2002 | Bentsen et al. ............... 264/1.6 |
| 6,451,191 B1 | 9/2002 | Bentsen et al. ............. 204/600 |
| 2002/0098124 A1 | 7/2002 | Bentsen et al. ............. 422/100 |

* cited by examiner

Primary Examiner—Jan M. Ludlow
(74) Attorney, Agent, or Firm—Stephen C. Macevicz

(57) ABSTRACT

A continuous form microstructure array device (20) is constructed as a flexible elongate film laminate containing microstructure arrays (26) arranged serially along the laminate. The laminate can be continuously drawn from a roll, passed through a processing and analysis device and rerolled or stacked for storage.

12 Claims, 14 Drawing Sheets

LAMINATE MICROSTRUCTURE DEVICE AND METHOD FOR MAKING SAME

This application is the National Stage Application of International Application No. PCT/US98/21869, filed Oct. 15, 1998, under 35 U.S.C. § 371, which claims benefit of, and is a continuation-in-part of U.S. patent application Ser. No. 08/950,403, filed Oct. 15, 1997.

BACKGROUND

This invention relates to methods and apparatus for high throughput sample analysis.

In a range of technology-based industries, including the chemical, bioscience, biomedical, and pharmaceutical industries, it has become increasingly desirable to develop capabilities for rapidly and reliably carrying out chemical and biochemical reactions in large numbers using small quantities of samples and reagents. Carrying out a massive screening program manually, for example, can be exceedingly time consuming and may be entirely impracticable where only a very small quantity of an important sample or component of interest is available, or where a component of a synthesis or analysis is very costly.

Developments in a variety of fields have resulted in an enormous increase in the numbers of targets and compounds that can be subjected to screening.

Rapid and widespread advances in the scientific understanding of critical cellular processes, for example, has led to rationally designed approaches in drug discovery. Molecular genetics and recombinant DNA technologies have made possible the isolation of many genes, and the proteins encoded by some of these show promise as targets for new drugs. Once a target is identified and the gene is cloned, the recombinant protein can be produced in a suitable expression system. Often receptors and enzymes exist in alternative forms, subtypes or isoforms and using a cloned target focuses the primary screen on the subtype appropriate for the disease. Agonists or antagonists can be identified and their selectivity can then be tested against the other known subtypes. The availability of such cloned genes and corresponding expression systems require screening methods that are specific, sensitive, and capable of automated very high throughput.

Similarly, an emergence of methods for highly parallel chemical synthesis has increased the need for high throughput screening ("HTS"). Conventionally, preparation of synthetic analogs to the prototypic lead compound was the established method for drug discovery. Natural products were usually isolated from soil microbes and cultured under a wide variety of conditions. The spectrum of organisms employed by the pharmaceutical industry for isolation of natural products has now expanded from actinomycetes and fungi to include plants, marine organisms, and insects. More recently, the chemistry of creating combinatorial libraries has vastly increased the number of synthetic compounds available for testing. Thousands to tens or hundreds of thousands of small molecules can be rapidly and economically synthesized. See, e.g., U.S. Pat. No. 5,252,743 for a discussion of combinatorial chemistry. Thus, combinatorial libraries complement the large numbers of synthetic compounds available from the more traditional drug discovery programs based, in part, on identifying lead compounds through natural product screening.

Accordingly, considerable resources have been directed to developing methods for high-throughput chemical syntheses, screening, and analyses. A considerable art has emerged, in part from such efforts.

Competitive binding assays, originally developed for immunodiagnostic applications, continue to be commonly employed for quantitatively characterizing receptor-ligand interactions. Despite advances in the development of spectrophotometric- and fluorometric-based bioanalytical assays, radiolabeled ligands are still commonly employed in pharmaceutical HTS applications. Although non-isotopic markers promise to be environmentally cleaner, safer, less expensive, and generally easier to use than radioactive compounds, sensitivity limitations have prevented these new methods from becoming widespread. Another major disadvantage of the competition assay is the number of steps, most notably washing steps, required to run assays.

Scintillation proximity assays, discussed for example in U.S. Pat. Nos. 4,271,139 and 4,382,074, were developed as a means of circumventing the wash steps required in the above heterogeneous assays. The homogeneous assay technology, which requires no separation of bound from free ligand, is based on the coating of scintillant beads with an acceptor molecule such as, for example, the target receptor.

In another approach to avoiding the use of radioactive labels, especially useful in high-throughput assays, lanthanide chelates are used in time-resolved fluorometry. See, e.g., U.S. Pat. No. 5,637,509.

Automated laboratory workstations have contributed significantly to advances in pharmaceutical drug discovery and genomic science. See, e.g., U.S. Pat. No. 5,104,621 and U.S. Pat. No. 5,356,525. Particularly, robotics technology has played a major role in providing practical means for carrying out HTS methods. See, e.g., U.S. Pat. No. 4,965,049.

Robotic-based high-throughput tools are now routinely used for screening libraries of compounds for the purpose of identifying lead molecules for their therapeutic potential. For example, a screening method for characterizing ligand binding to a given target employing a variety of separation techniques is described in WO 97/01755, and a related method is described in U.S. Pat. No. 5,585,277.

Highly parallel and automated methods for DNA synthesis and sequencing have also contributed significantly to the success of the human genome project, and a competitive industry has developed. Examples of automated DNA analysis and synthesis include, e.g., U.S. Pat. Nos. 5,455,008; 5,589,330; 5,599,695; 5,631,734; and 5,202,231.

Computerized data handling and analysis systems have also emerged with the commercial availability of high-throughput instrumentation for numerous life sciences research and development applications. Commercial software, including database and data management software, has become routine in order to efficiently handle the large amount of data being generated.

With the developments outlined above in molecular and cellular biology, combined with advancements in combinatorial chemistry, there has been a huge increase in the number of targets and compounds available for screening. In addition, many new human genes and their expressed proteins are being identified by the human genome project and will therefore greatly expand the pool of new targets for drug discovery. A great need exists for the development of more efficient ultrahigh throughput methods and instrumentation for pharmaceutical and genomic science screening applications.

Miniaturization of chemical analysis systems, employing semiconductor processing methods, including photolithography and other wafer fabrication techniques borrowed from the microelectronics industry, has attracted increasing attention and has progressed rapidly. The so-called "lab-on-a- chip" technology enables sample preparation and analysis to be carried out on-board microfluidic-based cassettes. Moving fluids through a network of interconnecting enclosed microchannels of capillary dimensions is possible using electrokinetic transport methods.

Applications of microfluidics technology embodied in the form of analytical devices has many attractive features for pharmaceutical high throughput screening. Advantages of miniaturization include greatly increased throughput and reduced costs, in addition to low consumption of both samples and reagents and system portability. Implementation of these developments in microfluidics and laboratory automation hold great promise for contributing to advancements in life sciences research and development.

Of particular interest are microfluidics devices in which very small volumes of fluids are manipulated in microstructures, including microcavities and microchannels of capillary dimension, at least in part by application of electrical fields to induce electrokinetic flow of materials within the microstructures. Application of an electric potential between electrodes contacting liquid media contained within a microchannel having cross-sectional dimensions in the range from about 1 $\mu$m to upwards of about 1 mm results in movement of the contents within the channel by electroosmotic flow and/or by electrophoresis. Electrophoresis is movement of electrically charged particles, aggregates, molecules or ions in the liquid medium toward or away from the electrodes. Electroosmotic flow is bulk fluid flow, including movement of the liquid medium and of dissolved or suspended materials in the liquid medium. The extent of bulk fluid flow resulting from application of a given electrical field depends among other factors upon the viscosity of the medium and on the electrical charge on the wall of the microchannel. Both electroosmotic flow and electrophoresis can be used to transport substances from one point to another within microchannel device.

Electrophoresis has become an indispensable analytical tool of the biotechnology and other industries, as it is used extensively in a variety of applications, including separation, identification and preparation of pure samples of nucleic acids, proteins, and carbohydrates; identification of a particular analyte in a complex mixture; and the like. Of increasing interest in the broader field of electrophoresis is capillary electrophoresis ("CE"), where particular entities or species are moved through a medium in an electrophoretic chamber of capillary dimensions under the influence of an applied electric field. Benefits of CE include rapid run times, high separation efficiency, small sample volumes, etc. Although CE was originally carried out in capillary tubes, of increasing interest is the practice of using microchannels or trenches of capillary dimension on a planar substrate, known as microchannel electrophoresis ("MCE"). CE and MCE are increasingly finding use in a number of different applications in both basic research and industrial processes, including analytical, biomedical, pharmaceutical, environmental, molecular, biological, food and clinical applications.

Typically, the microchannels of MCE devices are constructed by forming troughs or grooves of appropriate dimension and configuration in one surface of a planar rectangular- or disc-shaped base substrate, and applying a planar cover to the surface to enclose the microchannels.

Conventionally, microchannels having capillary dimensions have been made in silicon or glass substrates by micromachining, or by employing photolithographic techniques. See, e.g., U.S. Pat. Nos. 4,908,112, 5,250,263. Where the substrates are of fused silica, the microchannels can be enclosed by anodic bonding of a base and a cover. Exemplary MCE devices are also described in U.S. Pat. Nos. 5,126,022; 5,296,114; 5,180,480; and 5,132,012; and in Harrison el al., "Micromachining a Miniaturized Capillary Electrophoresis-Based Chemical Analysis System on a Chip," Science (1992) 261:895; Jacobsen et al., "Precolumn Reactions with Electrophoretic Analysis Integrated on a Microchip," Anal. Chem. (1994) 66:2949; Effenhauser et al., "High-Speed Separation of Antisense Oligonucleotides on a Micromachined Capillary Electrophoresis Device," Anal. Chem. (1994) 66:2949; and Woolley & Mathies, "Ultra-High-Speed DNA Fragment Separations Using Capillary Array Electrophoresis Chips," P.N.A.S. USA (1994) 91:11348.

Eckström et al. U.S. Pat. No. 5,376,252 describes a process for creating capillary size channels in plastic using elastomeric spacing layers. Öhman International Patent Publication WO 94/29400 describes a method for producing microchannel structures by applying a thin layer of a thermoplastic material to one or both of the surfaces to be joined, then joining the surfaces and heating the joined parts to melt the thermoplastic bonding layer. Kaltenbach el al. U.S. Pat. No. 5,500,071 describes constructing a miniaturized planar microcolumn liquid phase analytical device by laser ablating microstructures in the surface of a planar laser ablatable polymeric or ceramic substrate, rather than by conventional silicon micromachining or etching techniques.

U.S. Pat. No. 6,176,962 describes methods for fabricating microchannel structures constructed of a polymeric card-shaped or disc-shaped base plate having a planar surface in which a microchannel structure is formed, and a planar polymeric cover. The microchannel structure is enclosed by bonding the planar surfaces of the cover and the base plate together.

SUMMARY OF THE INVENTION

In one general aspect, the invention features a continuous form microstructure (i.e., microcavity and/or microchannel) array device constructed as an elongate flexible film laminate containing a plurality of microstructures or arrays of microstructures arranged serially lengthwise along the laminate. Where the device has a series of microstructures, each structure is configured to carry out a fluidic process or a step in a fluidic process. Where the device has a series of microchannel arrays, each array is configured to carry out a set of processes or steps, on an array of samples or of test reagents.

Because the microstructures, or arrays of microstructures, are serially arranged lengthwise along the laminate, the device can be fed lengthwise into and through an analytical device, and the structures or arrays can be treated serially in a continuous automated or semiautomated manner.

In some embodiments the flexible elongate laminate device is advanced within the analytic device from a continuous uncut supply roll, through the various parts of the analytical device and, as the laminate device is expended, to a takeup roll, similar to the way in which roll film is advanced frame-by-frame through a camera. In other embodiments the elongate laminate device is advanced within the analytic device from a continuous uncut accordion-folded supply stack, through the analytical device and, as the laminate device is expended, to an accordion-folded takeup stack. When the entire roll (or supply stack) has been expended and passed onto the takeup roll (or stack), the expended roll (or stack) can be discarded, or can conveniently and efficiently be stored in an archive, as may be desirable for some uses.

The microstructures are constructed either by forming channels, trenches or cavities of suitable dimension and configuration in a microchannel surface of a first lamina and, optionally, enclosing the channels by apposing a covering surface of a second lamina onto the microchannel surface to form the microstructures; by forming slits having suitable dimension and configuration in a spacing lamina, and sandwiching the spacing lamina between first and second enclosing laminae to enclose the slits between the apposed surfaces of the first and second enclosing laminae to form the microchannels or by combining a spacing lamina having slits therein with a lamina having such channels, trenches or cavities formed therein.

Electrodes can be formed in the device by any of a variety of techniques, known in the art, including application of wires or conductive decals, or printing or stamping using conductive inks, or vapor deposition, etc., in a specific configuration onto a surface of one or both of the laminae. The laminate construction according to the invention is particularly suitable for application of flexible printed circuit technology. For technical review, See, Th. H. Stearns (1996), Flexible Printed Circuitry, SMTnet Bookstore. See also, U.S. Pat. No. 4,626,462; U.S. Pat. No. 4,675,786; U.S. Pat. No. 4,715,928; U.S. Pat. No. 4,812,213; U.S. Pat. No. 5,219,640; U.S. Pat. No. 5,615,088.

Processes for making flexible printed circuits are generally well known. Briefly, the electrodes, which provide connections from the reservoirs in the microfluidic structure to high-voltage contacts in an analytical device that carried the laminate, are formed within a thin polymer film laminate, which serves as a cover lamina to be affixed as described above to the base lamina, as described in more detail below.

In this context, an "analytical device" is a device that includes at least a detector capable of detecting or of measuring a signal produced in the course of the microfluidic process or process step, and means for moving the laminate in relation to the analytical device to bring a detection region in the microstructure within the field of the detector. Usually the analytical device is in a stable installation, and the laminate is advanced through it past the detector, but in some embodiments the laminate is held in place and the analytical device is moved along it. Of course, any number of such detectors may be employed, each alignable with a detection region (or series of detection regions, as the laminate progresses through). Usually, the analytical device also includes electrical contacts each alignable with a contact point in electrical circuitry employed to generate electroflow in the microstructure. Each such contact is electrically connected to a source of electrical power, and to control means (which may be automated) for changing the applied electric fields as the microfluidic process proceeds. The analytical device may further include means for adding various fluids (e.g., samples, buffers or other solvents, reagents, and the like) to the microstructures by way of access ports in the laminate. The analytical device may additionally include means for changing the environmental conditions surrounding a portion of the laminate, such as temperature, and the like.

In some embodiments, the device is provided as an assembled laminate, in which the microchannels are fully enclosed; and in which ports or reservoirs are provided for introduction of sample or reagents or test compounds or liquid media; and in which electrodes have been emplaced and provided with leads for connection to a source of electrical power. Reagents, samples, test compounds, and/or media can be introduced as appropriate during or just prior to conducting the assays. In some embodiments the assembled laminate is provided with at least some of the media or reagents "on board" in the microchannels or reservoirs as appropriate. Where the device is provided with one or more substances already on board, the device can additionally be provided with means for protection of degradable contents from variations in ambient conditions and, particularly, for example, a release liner which resists loss of moisture or of volatile contents and/or which resists light exposure to the contents, may be provided as a release liner on one or both surfaces of the laminate.

The device and method of the invention provides a full range of advantages in analytical sensitivity that inhere in the use of conventional microfluidic analysis, while at the same time providing for automated or semiautomated continuous processing of high numbers of analyses at high rates of speed. The complexity of mass screening programs, for example, is substantially reduced by elimination of many of the manipulation steps, whether by hand or by machine, that are required in use of conventional assay plates. And possibilities for error are reduced by reduction of the number of points at which manipulation by hand is required.

Methods and apparatus according to the invention for carrying out multiple microfluidic manipulations at high throughput rates are readily adaptable for automated noncontact dispensing of reagents or samples, providing for substantially reduced risk of cross-contamination.

Further, the continuous form assay array according to the invention significantly reduces the bulk volume of disposable materials, as compared with conventional assay card methods, both because the flexible laminates themselves are thinner than are conventional assay cards, and because the microchannel structures or arrays can be arranged on the continuous form device with more efficient use of the substrate surface area.

BRIEF DESCRIPTION OF THE DRAWINGS

FIG. 11b is a diagrammatic sketch of a portion of the length of flexible circuit laminate showing two in a series of layouts of electrodes and electrical contacts, each layout configured to serve a microchannel array as shown in FIG. 11a.

FIG. 11c is a diagrammatic sketch of a portion of the length of an embodiment of a continuous form elongate laminate microstructure device of the invention, constructed by laminating the flexible circuit laminate of FIG. 11b onto the base lamina of FIG. 11a.

Figure 1A:
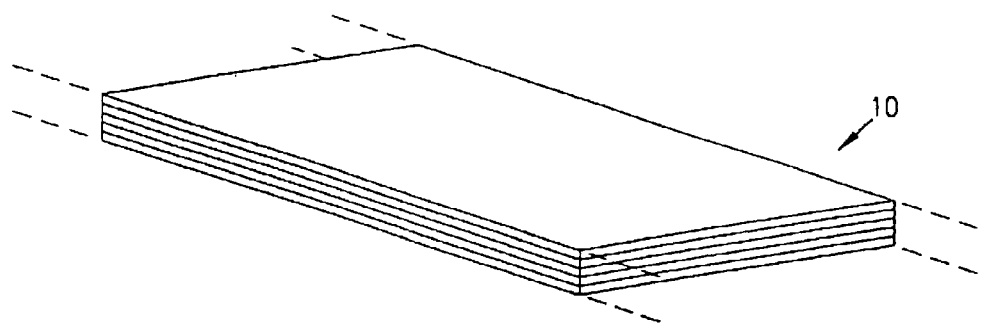
FIG. 1A is a diagrammatic sketch showing a portion of an embodiment of the laminate construction of a continuous form microchannel device of the invention.

The drawings are diagrammatic only and not to scale and, particularly, in some of the Figs. the thicknesses of the laminate composites and of the layers of which they are constructed are much exaggerated for clarity of presentation.

DETAILED DESCRIPTION

Construction

In General

"Microfluidic processing", as that term is used herein, means and refers to fluid processing—that is, fluid handling, transport and manipulation—carried out within chambers and channels of capillary dimension. Valveless sample injection is achieved by moving fluid from reagent reservoirs into cross-channel injection zones, where plugs of buffer or test compounds are precisely metered and dispensed into a desired flowpath. The rate and timing of movement of the fluids in the various microchannels can be controlled by electrokinetic, magnetic, pneumatic, and/or thermal-gradient driven transport, among others. These sample manipulation methods enable the profile and volume of the fluid plug to be controlled over a range of sizes with high reproducibility. In addition, microfluidic processing includes sample preparation and isolation where enrichment microchannels containing separation media are employed for target capture and purification. Microfluidic processing also includes reagent mixing, reaction/incubation, separations and sample detection and analyses.

Generally, the expression "microstructure", as used herein, means and refers to a single enclosed microchannel or a network of interconnecting microchannels having cross-sectional dimensions suitable for carrying out microfluidic manipulations of materials carried by them. Several steps or stages of an analytical process may be carried out in one microchannel structure, suitably configured. Configurations of various complexity are disclosed for example in U.S. Pat. Nos. 5,900,130 and 6,007,690, the entire contents of each of which are incorporated herein by this reference.

A "microfluidic network", as that term is used herein, is a system of interconnected microchannels, i.e., cavity structures and capillary-size channels, through which fluids can be manipulated and processed.

Cavity structures, in the context of microstructures, are spaces, usually formed in, e.g., a planar substrate, a plate, or the like in accordance with the present invention. Cavity structures include, e.g., wells, reservoirs, chambers for incubation or separation or detection, and the like. Cavity structures can be present at one or both of the termini, i.e., either end, of a channel, and are there usually referred to as reservoirs. Such cavities structures may serve a variety of purposes, such as, for example, means for introducing a buffer solution, elution solvent, reagent rinse and wash solutions, and so forth into a main channel or one or more interconnected auxiliary channels, receiving waste fluid from the main channel, and the like. In some embodiments, cavity structures are not connected by channels, but rather stand alone; such free standing cavities can be used for reagent introduction, on-board mixing, incubation, reactions, detection and the like. In another embodiment, these individual steps of a homogeneous assay can be carried out in a cavity.

In the microstructures of the invention "channels", usually "microchannels", provide conduits or means of communication (usually fluid communication and more particularly liquid communication), between cavity structures and the like. Channels include capillaries, grooves, trenches, microflumes, and so forth. The channels may be straight, curved, serpentine, labyrinth-like or other convenient configuration within the planar substrate. The cross-sectional shape of the channel may be circular, ellipsoidal, trapezoidal, square, rectangular, triangular and the like within the planar substrate in which it is present.

The inside of the channel may be coated with a material to improve the strength of the microstructure, for modifying, enhancing or reducing electroosmotic flow, for enhancing or reducing electrophoretic flow, for modification of surface hydrophobicity/hydrophilicity, for binding of selected compounds, and so forth. Exemplary coatings are silylation, polyacrylamine (vinyl-bound), methylcellulose, poleyther, polyvinylpyrrolidone, and polyethylene glycol, polypropylene, Teflon™ (DuPont), Nafion™ (DuPont), polystrene sulfonate and the like may also be used. See also U.S. Pat. No. 5,935,401, the relevant disclosure of which is incorporated herein by reference.

A "microchannel", as that term is used herein, is an at least partly enclosed trench or channel or cavity having capillary dimensions, that is, having cross-sectional dimensions that provide for capillary flow along the channel. Usually at least one of the cross-sectional dimensions, e.g., width, height, diameter, is at least about 1 µm, usually at least 10 µm; and is usually no more than 500 µm, preferably no more than 200 µm. Channels of capillary dimension typically have an inside bore diameter ("ID") of from about 10 to 200 microns, more typically from about 25 to 100 microns.

Microchannels can provide for electroflow between cavity structures and the like in the microstructures of the invention. "Electroflow", as used herein, is the manipulation of entities such as molecules, particles, cells, vitreous fluid and the like through a medium under the influence of an applied electric field by use of electrodes and the like to induce movement such as electrokinetic flow, electroosmotic flow, electrophoretic flow, dielectrophoretic flow, and so forth. Depending upon the nature of the entities, e.g., whether or not they carry an electrical charge, as well as upon the surface chemistry of the chamber in which the electroflow is conducted, the entities may be moved through the medium under the direct influence of the applied electric field or as a result of bulk fluid flow through the pathway resulting from the application of the electric field, e.g., electroosmotic flow. It is within the purview of the present invention that electroflow can be carried out in conjunction with movement of material by other means than application of an electric field, such as by gravity or by application of a magnetic field, centrifugal force, thermal gradients, aspiration, negative pressure, pumping, pneumatic forces, and the like.

An "electroflow medium" is an electrically conductive medium, that is generally utilized in carrying out microfluidic processes. The particular medium chosen is one that is suitable to a particular application of the present invention. Such media include, for example, buffer solutions, cross-linked and uncross-linked polymeric solutions, organic solvents, detergents, surfactant micellular dispersions, gels of the type generally used in connection with analytical separation techniques and other microfluidic processes, and so forth. For example, cross-linked polyacrylamide gel, cellulose derivatives, uncross-linked polyacrylamide and derivatives thereof, polyvinyl alcohols, polyethylene oxides and the like may be used. For a discussion of such media see, e.g., Barron and Blanch. "DNA Separations by Slab Gel and Capillary Electrophoresis: Theory and Practice", Separation and Purification Methods (1995) 24:1–118.

Suitable electroflow media include conventional buffers such as, for example, the Good's buffers (HEPES, MOPS, MES, Tricine, etc.), and other organic buffers (Tris, acetate, citrate, and formate), including standard inorganic compounds (phosphate, borate, etc.). Exemplary buffer systems include: (i) 100 mM sodium phosphate, pH 7.2; (ii) 89.5 mM tris-base, 89:5 mM Boric acid, 2 mM ETDA, pH 8.3. Buffer additives include: methanol, metal ions, urea, surfactants, and zwitterions, intercalating dyes and other labeling reagents. Polymers can be added to create a sieving buffer for the differential separation of molecular species, such as, e.g., nucleic acids, proteins, and the like, based on molecular size. Examples of such polymers are: polyacrylamide (cross-linked or linear), agarose, methylcellulose and derivatives, dextrans, and polyethylene glycol. Inert polymers can be added to the separation buffer to stabilize the separation matrix against factors such as convective mixing.

Alternatively, buffers containing micelles can be used for effecting separation of electrically neutral or hydrophobic substances of interest. The micelles are formed in the buffer by addition of an appropriate surfactant at a concentration exceeding the critical micelle concentration of that detergent. Useful surfactants include but are not limited to sodium dodecyl sulfate, dodecyltrimethyl ammonium bromide, etc. Weakly charged or apolar analytes partition into the micelles to different degrees depending upon their degree of hydrophobicity and thus can be separated. This subtechnique of capillary electrophoresis is termed micellar electrokinetic chromatography.

"Electrophoresis" is separation of components in a liquid by electroflow. Various forms of electrophoresis include, by way of example and not limitation, free zone electrophoresis, gel electrophoresis, isotachophoresis, high performance CE, capillary zone electrophoresis, and the like. In the context of the microstructures according to the invention, an "electrophoresis column" is a channel for carrying out electrophoresis.

A microstructure can be made by forming one or more trenches or channels or cavities in the desired configuration and with the desired dimensions in one surface of a lamina, and then optionally covering selected portions at least of the trenches or channels or cavities with a second lamina to form one or more enclosed microchannels. Or, a microstructure can be made by forming slits in the desired configuration and with the desired dimensions through a spacing lamina having a desired thickness, and then enclosing selected portions at least of the slits by sandwiching the spacing lamina between two enclosing laminae to form one or more enclosed microchannels.

As noted above, the enclosed volumes within the microchannels provide "flow paths", in which the various components of the analytical process can move and combine and interact or react, and in which analytes can be separated electrophoretically or retained by capture media. Any of a variety of means can be employed to provide sources of supply of the various components to the flow paths.

Any of a variety of means can be employed to cause movement of the various components within the microchannels. Usually, as noted above, an electric field is applied to a segment of a microchannel to cause electrokinetic transport (by electroosmotic flow or by electrophoresis, or by some combination of EOF and electrophoresis) of the contents of the microchannel segment. An electric field can be applied by positioning a pair of electrodes, connected to a source of electrical power, within the microchannel at the ends of the microchannel segment. Where it is desired, for example, to move a buffer from a buffer reservoir along a microchannel to a buffer waste reservoir, the pair of electrodes can be positioned so that they contact the fluid within the respective reservoirs; application of an electric potential across the electrodes induces a electrokinetic flow from one reservoir to the other through the microchannel.

Additionally, as noted above, other means than electrokinetic flow may be used to move the components within the microchannels, and, particularly, to fill the microchannel structure at the outset, or to introduce an aliquot of sample material or of a test compound, for example, at the beginning of or in the course of the analysis.

As used herein, the expression "array of microchannel structures" means and refers to a set of microchannel structures, typically but not necessarily all having the same or similar configurations, each operating to carry out one of a set of related analyses, as will be described more fully below. A microstructure or an array of microstructures can according to the invention be arranged within the laminate structure so that the positions of various of the cavities correspond to particular useful sites in conventional sample holding or sample delivery apparatus. Thus, for example, certain of the cavities may be arranged and spaced apart to correspond to the dimensions and configurations of a standard multiwell plate, which has an array of wells. Standard plates may have any number of wells, usually in a pattern, and usually numbering 96, 192, 384 or 1536 wells or more. Examples of such multiwell plates are microtiter plates having a pattern of wells. The wells extend into the substrate forming the plate, and are open at the top surface of the plate and closed at the bottom. There are no openings, holes or other exits from the wells other than from the top surface at the opening of the well. Similarly, a transfer plate may have a like arrangement of apertures or nozzles, and at least selected ones of the cavities in the microstructure or microstructure array according to the invention can accordingly be arranged so that direct transfer can be made from the plate to the microcavity network.

Other arrangements for the arrays of microchannel structures are possible, according to the particular dispensing requirements, among other factors. For example, an array of 96 microstructures may be in a 12×8 orthogonal arrangement, corresponding to the positions of wells in a 96-well microtiter plate; or in a linear arrangement of 96 microstructures, or any other arrangement. And, an array of 384 microstructures may be in a 24×16 orthogonal arrangement, corresponding to the positions of wells in a 384-well microtiter plate; or in a linear arrangement of 384 microstructures, or any other arrangement.

Depending upon the type of analysis to be performed, any of various liquid media including buffers or solvents or electrophoretic separation media, reagents, etc., may be brought into play in the course of the analysis.

At one or more points in the analytical process, detection and/or measurement of one or more analytes is required. The analyte or analytes may be, for example, a plurality of electrophoretically resolved reaction products, such as restriction fragments of a nucleic acid, bound and free fractions in a ligand-binding assay, substrate and product of an enzymatic reaction, and the like.

The Laminate

Figure 1B:
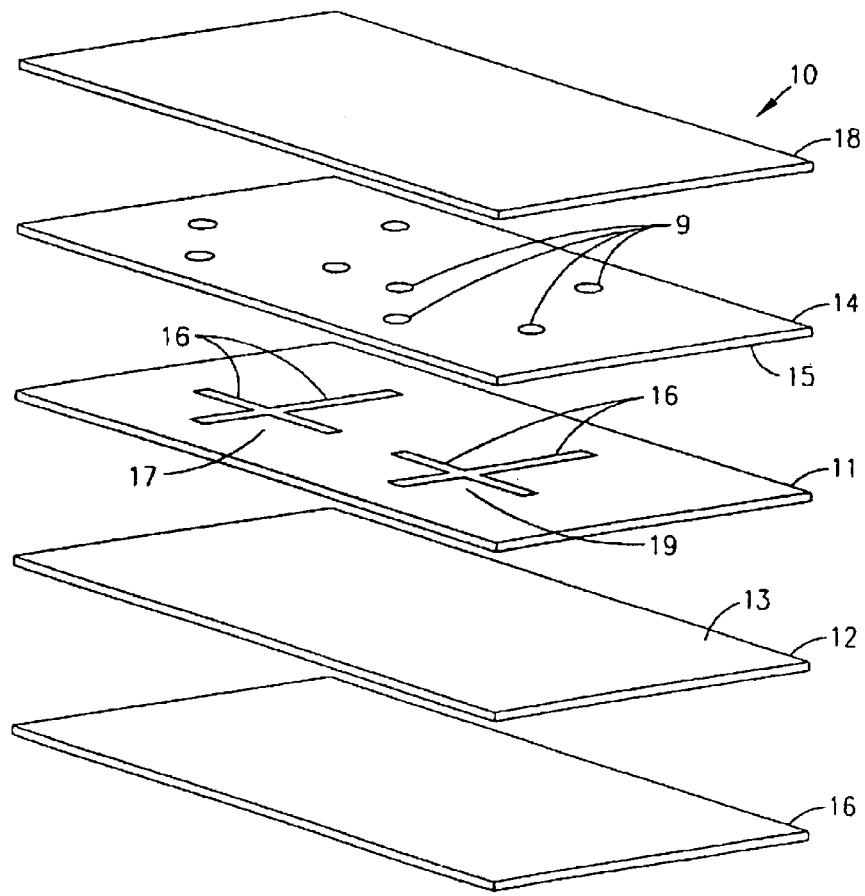
FIG. 1B is a diagrammatic sketch of the portion of the embodiment of FIG. 1A, in an exploded view, showing the laminae.

Referring now to FIGS. 1A, 1B, there is shown at 10 a portion of an embodiment of an elongate flexible film laminate or microstructure device according to the invention, as assembled (FIG. 1A) and in an exploded view in which the laminae appear as separated (FIG. 1B). In FIGS. 1A and 1B, as in FIGS. 2A, 2B, only a short segment of the full length of the laminate is shown, as suggested by broken lines indicating that the laminate extends lengthwise beyond the margins of the drawing. In the embodiment of FIGS. 1A, 1B, the microchannel structure is formed in a spacing lamina 11 sandwiched between a base lamina 12 and a cover lamina 14. Slits 16 having capillary cross-sectional dimensions are formed through spacing to lamina 11, and are enclosed by apposed surfaces 13, 15 of base lamina 12 and cover lamina 14 in the composite structure. FIG. 1B shows slits forming walls of just two 17, 19 of many microchannel structures serially arranged lengthwise on the elongate laminate. In the example shown in FIGS. 1A, 1B, each microchannel structure has a simple cross configuration formed by enclosure of a pair of intersecting slits.

As will be appreciated, the widths of the microchannels resulting from the construction illustrated in FIGS. 1A, 1B is established by the width of the slits in the spacing lamina; and the thickness of the microchannels is established by the distance between the apposed surfaces 13, 15 of the enclosing laminae 12 and 14, which approximates the thickness of the spacing layer. As noted above, the microchannels are of capillary dimension, that is, the larger cross-sectional dimension (usually the width) of the microchannel is usually no greater than about 750 μm, more usually no greater than about 500 μm, and most usually in the range from about 100 μm to about 250 μm; and the smaller cross-sectional dimension (usually the depth) can be somewhat smaller.

Usually, as noted generally above, reservoirs or access ports or receptacles are provided for introducing the various components of the analytic process (sample, buffers or solvents, test compounds, etc.) into the microchannel structures. These can be in the form, for example, of perforations 9 through the base lamina 12 or through the cover lamina 14, as illustrated in FIG. 1B. Where, as shown for example in FIG. 1B, the reservoirs or access ports or receptacles are formed in a lamina other than the one in which the channels are formed, they must be located so as to be suitably aligned with appropriate sites in the microchannel structure when the composite is assembled. Accordingly, in FIG. 1B, the perforations 9 in the cover lamina 12 are arranged to be aligned with the ends of the microchannels formed in the spacing layer 11 when the spacing lamina 11 is sandwiched between the apposed surfaces 13, 15 of the base lamina 12 and the cover lamina 14.

To provide for predictable and consistent microfluidic movement, mixing, and separations, the microchannels in the laminate composite device must be adequately dimensionally stable, and the apposing surfaces 13, 15 of the enclosing laminae 12, 14 must be adequately sealed to the surfaces of spacing lamina 11, at least at the margins of the slits, to keep the fluids within the flow paths formed by the microchannels from escaping between the laminae. These requirements are met by appropriate selection of materials and thicknesses of the films making up the laminae, and by appropriate selection of means for sealing the contact surfaces of the laminae.

As noted above, each of the laminae is a flexible film, usually firm enough to hold the shape and dimensions of the microchannels, yet sufficiently compliant to provide a desired flexibility in the composite laminate device. Preferred films include acrylics and polyethylenes, for example. Preferred means for sealing will be selected according to the film materials in the laminae to be joined. Particularly, for example, the film materials and adhesives described in U.S. Ser. No. 08/878,437 filed Jun. 18, 1997, the disclosure of which is hereby incorporated herein in its entirety.

In the embodiment of FIGS. 1A, 1B, the thickness of the spacing lamina is selected to provide the desired microchannel depth, taking into account any effect (additive or subtractive) that the sealing process may have on the distance between the apposed surfaces 13, 15 of the enclosing laminae.

In addition to the spacing lamina 11 and the enclosing laminae 12, 14, the laminate may further include release liners 16 and/or 18. Use of a release liner may be especially desirable where at least some of the components of the analytical process (a reagent or a buffer, for example) are provided on board the device prior to use. Such release liners can mitigate degradation or loss of the contents of the device during prolonged exposure to varying environmental conditions that may be encountered prior to use of the device, as for example during storage. It may be particularly important, for example, to avoid loss or intrusion of moisture or of more volatile substances out from or into the microchannel structure. Or, it may be important to avoid exposure to light. Accordingly, preferred release liners form a barrier to movement of moisture or volatile materials, and thin polymer films, including metallized films may be particularly suitable.

Figure 2A:
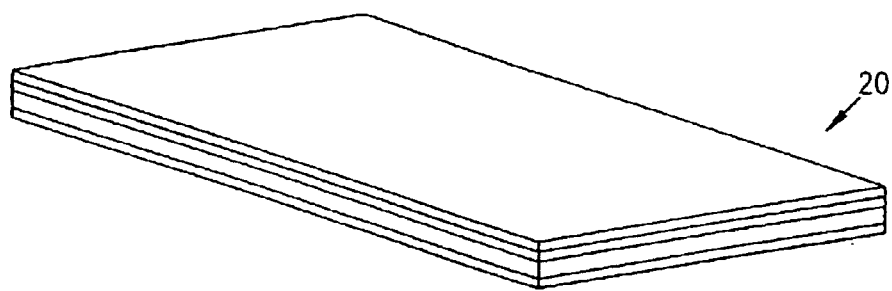
FIG. 2A is a diagrammatic sketch of a portion of an alternate embodiment of the laminate construction of a continuous form microchannel device of the invention.
Figure 2B:
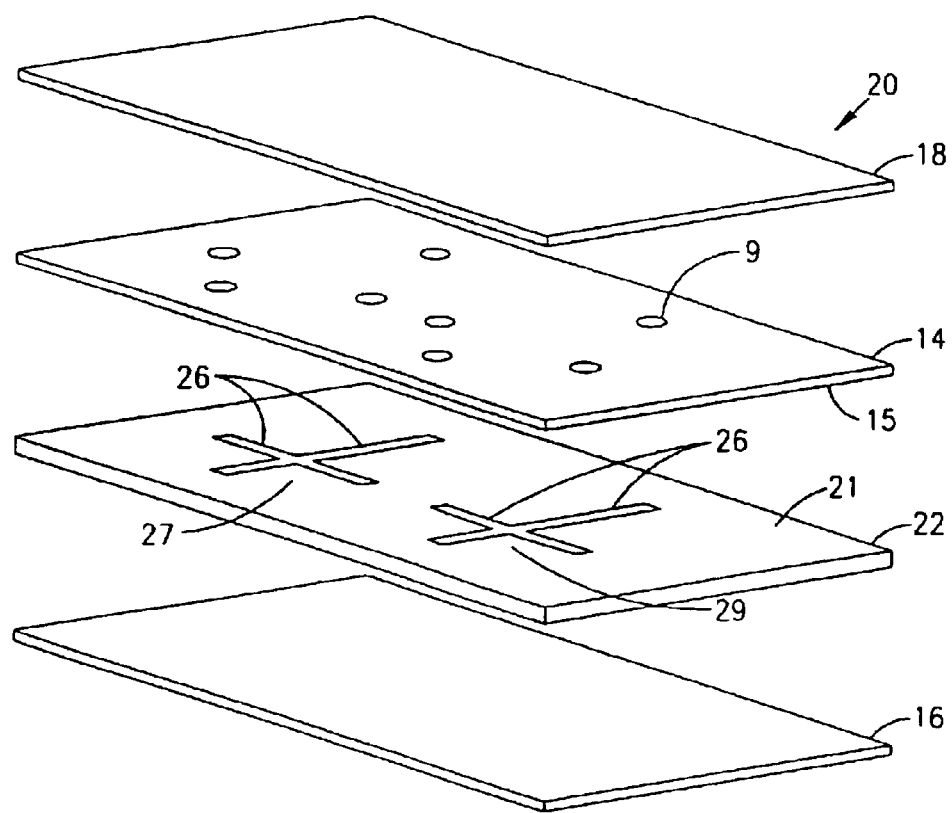
FIG. 2B is a diagrammatic sketch of the portion of the embodiment of FIG. 2A, in an exploded view, showing the laminae.

Referring now to FIGS. 2A, 2B, there is shown at 20 a portion of an alternate embodiment of an elongate flexible film laminate or microstructure device according to the invention, a assembled (FIG. 2A) and in an exploded view in which the laminae appear as separated (FIG. 2B). In this embodiment, the microchannel structures 27,29 are constructed by forming channels or trenches 26 in a surface 21 of base lamina 22, and apposing a surface 15 of a cover lamina 14 onto surface 21 to enclose the microchannels. Reservoirs or access ports or receptacles can be provided for introduction of process components into and/or for removal of excess or waste from the microchannel structure, as noted with reference to FIGS. 1A, 1B. These are illustrated by way of example in FIG. 2A as perforations 9 through cover lamina 14, positioned so as to be suitably aligned with the channels or trenches 26 in the base lamina 22 when the surfaces 21, 15 of base lamina 22 and cover lamina 14 are apposed.

Alternatively, reservoirs may be provided in base lamina 22, in the form of wells or holes through the thickness of base lamina 22, each situated in fluid communication with a microchannel or trench, as may be desired. And, referring again to FIGS. 1A, 1B, reservoirs may be provided in the spacing lamina 11, each in fluid communication with a slit. If the base lamina 22 (or the spacing lamina 11) is sufficiently thick, reservoirs of significantly high volume can be provided in this way, and the cover lamina (or enclosing laminae) can be very thin. For reservoirs that are loaded in the course of the lamination process, no access opening through either the cover lamina or the opposite surface of the base lamina (or either of the spacing laminae) is required; however, for any such reservoirs that are to be loaded after the laminate has been formed, access openings aligned with the reservoirs can be provided, for example as holes through the cover lamina or through the base lamina (or through a spacing lamina).

In this embodiment the widths and depths of the microchannels are established by the dimensions of the trenches or channels formed in the base lamina. Accordingly, precise control of the dimensions during the formation of the trenches or channels, taking account of any additive or subtractive effect of the sealing process, results in reproducible microchannel dimensions.

As in the embodiment of FIGS. 1A, 1B, the embodiment of FIGS. 2A, 2B may additionally include release liners 16 and/or 18.

As in the embodiment of FIGS. 1A, 1B, each of the laminae in the embodiment of FIGS. 2A, 2B is a flexible film. Preferred film materials for the base lamina 22 and cover lamina 14 are polymer films; and preferred sealing means are selected according to the film materials to be joined. The base lamina 12 preferably is sufficiently thick to maintain its structural integrity after the trenches or channels have been formed in it. Particularly, for example, where the configuration of the microchannel structure is complex, or where there is a high density of trenches or channels, the mechanical strength of the base lamina may be compromised, and for ease of handling as well as to maintain the dimensionality of the microchannel structure during assembly and use, the base lamina should be thick enough so that it maintains its mechanical integrity.

Detection is usually optical, and most usually the signal is generated by laser-induced fluorescence; the detector is usually a conventional confocal optical system. Other detections means may be employed.

Figure 3C:
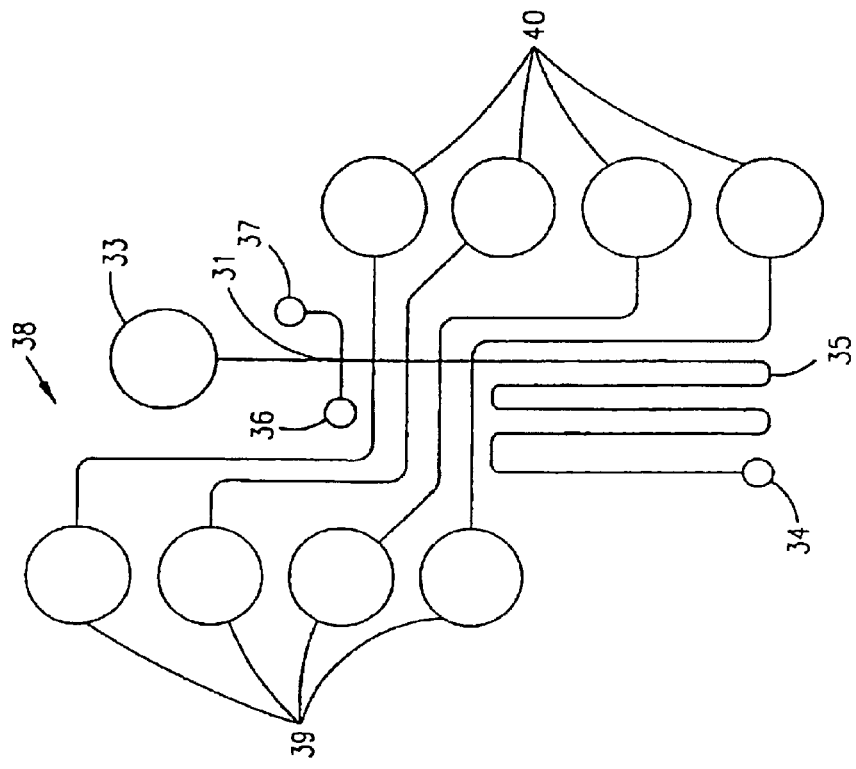
FIG. 3C is a diagrammatic sketch in plan view of an embodiment of a microchannel structure providing for introduction of four reagents into a sample flow path upstream from the separation channel, which is folded to provide extended separation flow path length.
Figure 3B:
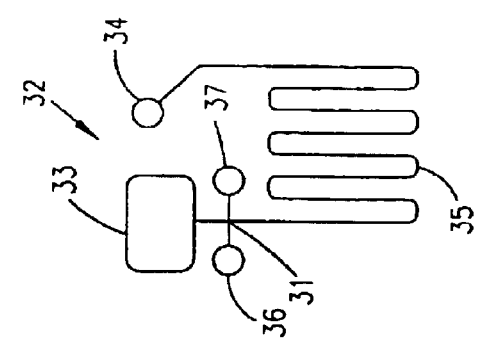
FIGS. 3A, 3B are diagrammatic sketches in plan view of two alternative embodiments of microchannel structures configured as standard injection crosses, in which the separation channel is curved (FIG. 3A) or folded (FIG. 3B) to provide extended separation flow path length.
Figure 3A:
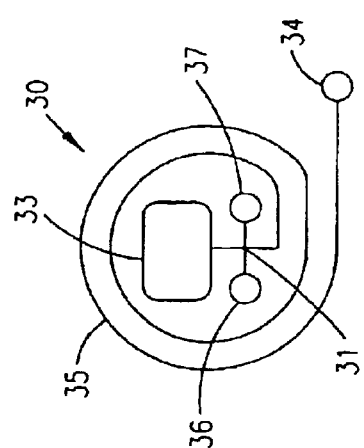

As noted above, each of the microchannel structures shown in FIGS. 1B, 2B is configured as a simple injection cross, formed by intersection of two straight microchannels. Such a configuration is useful, for example, in carrying out a quantitative electrophoretic separation of a metered sample volume, as described for example in U.S. patent application Ser. No. 08/878,447 filed Jun. 18, 1997 [SOAN-017]. The intersecting microchannels of a simple injection cross need not be straight, and in some configurations more efficient use of the substrate area is made possible by configuring one or more microchannel arms otherwise. Referring now for example to FIGS. 3A, 3B, alternative embodiments of simple injection cross configurations are shown in which one electrophoretic microchannel is made relatively longer. In each of microchannel structure configurations or microstructures 30, 32, a shorter microchannel and a longer microchannel intersect at 31 to form an injection cross. Sample supply reservoir 36, sample drain reservoir 37, elution buffer reservoir 33, and analyte waste reservoir 34 are provided at the ends of the microchannel segments; and an electrode (not shown in the Figs.) connected to a source of electrical energy is positioned to contact the liquid contained within each reservoir. Potential differences across the electrodes are adjusted first to draw the sample electrokinetically from sample supply reservoir 36 across intersection 31 toward sample drain reservoir 37; and then to draw a metered volume of sample from intersection 31 into separation channel 35. As the sample plug proceed electrokinetically through separation channel 35 toward analyte waste reservoir 34, the sample becomes electrophoretically separated into its analyte components, which are detected at a downstream detection region point in separation channel 35. As will be apparent in the Figs., the electrophoretic separation channel is made relatively much longer by forming it as a spiral turning one or more times around intersection 31 and reservoirs 33, 36, 37, and the shorter microchannel arms (FIG. 3A), or by forming it in a folded configuration (FIG. 3B). The resulting microchannel structures occupy a compact area of the substrate, and can be particulay useful in microchannel arrays, as will be described more fully below with reference to FIG. 4.

The microchannel structures can be formed in more complex configurations, according to the analytical process to be carreid out in them. Referring now to FIG. 3C, there is shown by way of example at 38 a microchannel structure or microstructure having an intersection 31 forming an injection cross, and having sample supply reservoir 36, sample rain reservoir 37, elution buffer reservoir 33, and extended electrophoretic separation channel 35 leading to waste reservoir 34. In this embodiment, microchannels enclosing flow paths running from four additional supply reservoirs 39 to four additional downstream drains 40 additionally cross the microchannel downstream from the intersection 31. These additional flow paths provide for sequential introduction of four additional analytical components (which may be reagents, or test compounds, or buffers, etc.) to the moving sample plug.

Figure 4:
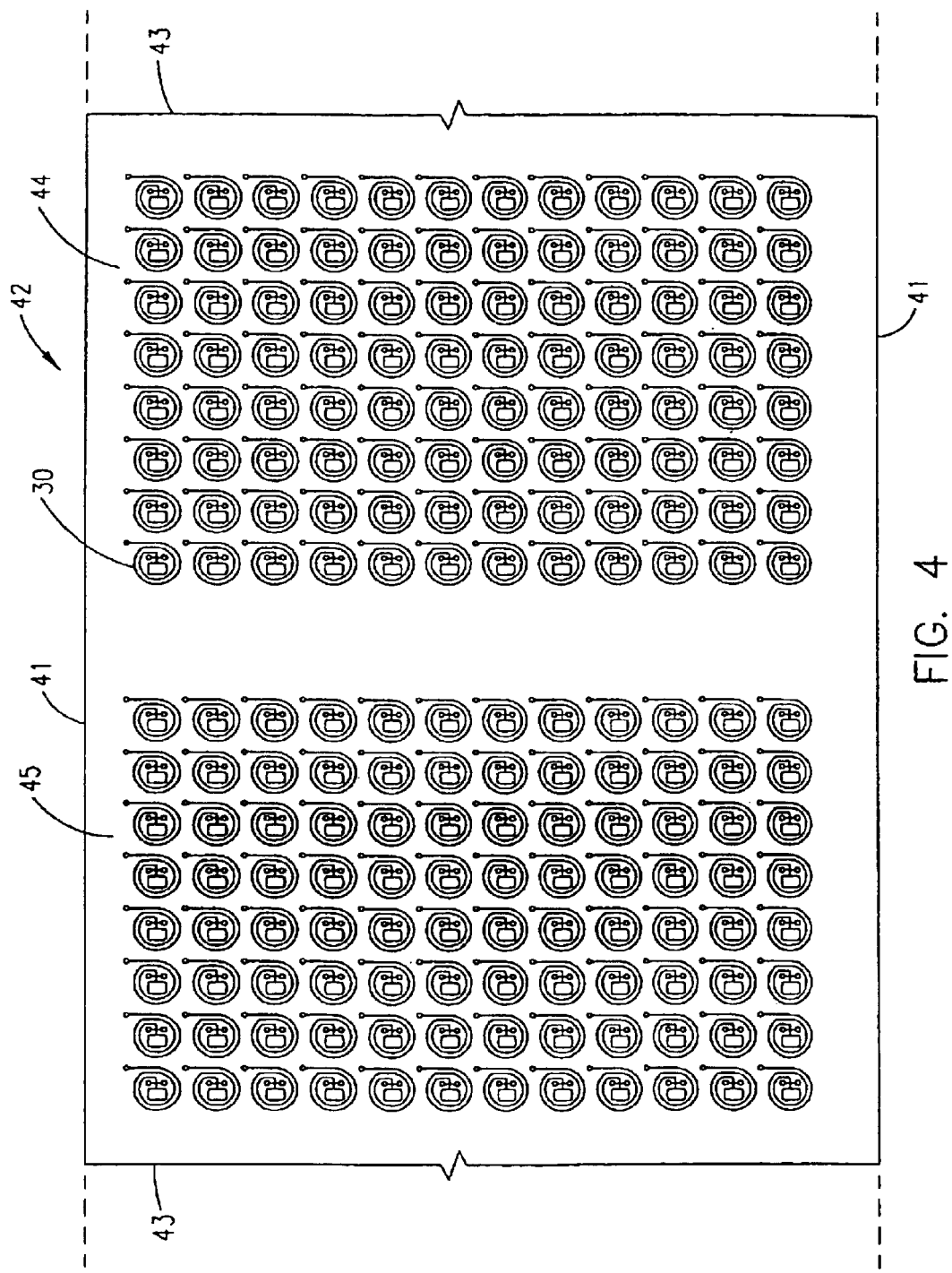
FIG. 4 is a diagrammatic sketch in plan view of a portion of the length of an embodiment of a continuous form microchannel device of the invention, showing two in a series of microchannel arrays.

An example of a microchannel array is shown in a plan view in FIG. 4, illustrating a way in which the arrangement of the microchannels structures in the array can be made to match the geometry of, for example, a standard 96-well plate. Such an arrangement can facilitate automated transfer of samples or of test compounds from the standard plate to the continuous form microchannel device of the invention, providing for efficient transfer with reduced waste and minimal cross-contamination. FIG. 4, for example, shows a short segment of an elongate flexible film laminate containing a series of microchannel arrays according to the invention. The elongate flexible film laminate 42 extends lengthwise beyond the range of the drawing, as indicated by broken lines extending from the edges 41 of the short segment. The short segment shown, which is limited by lines 43, includes two successive microchannel arrays or microstructures 44, 45. Each of the microchannel arrays 44, 45 in this example contains 96 microchannel structures 30, each configured as in the example shown in FIG. 3A, and all arranged in an orthogonal 12×8 grid that conforms to the geometry of a conventional 96-well plate.

Manufacture

The basic technique and machinery for bringing the laminae together to form the laminate composite according to the invention are generally known, and, depending upon the materials that make up the various laminae, any of a variety of film lamination techniques can be used.

Figure 5:
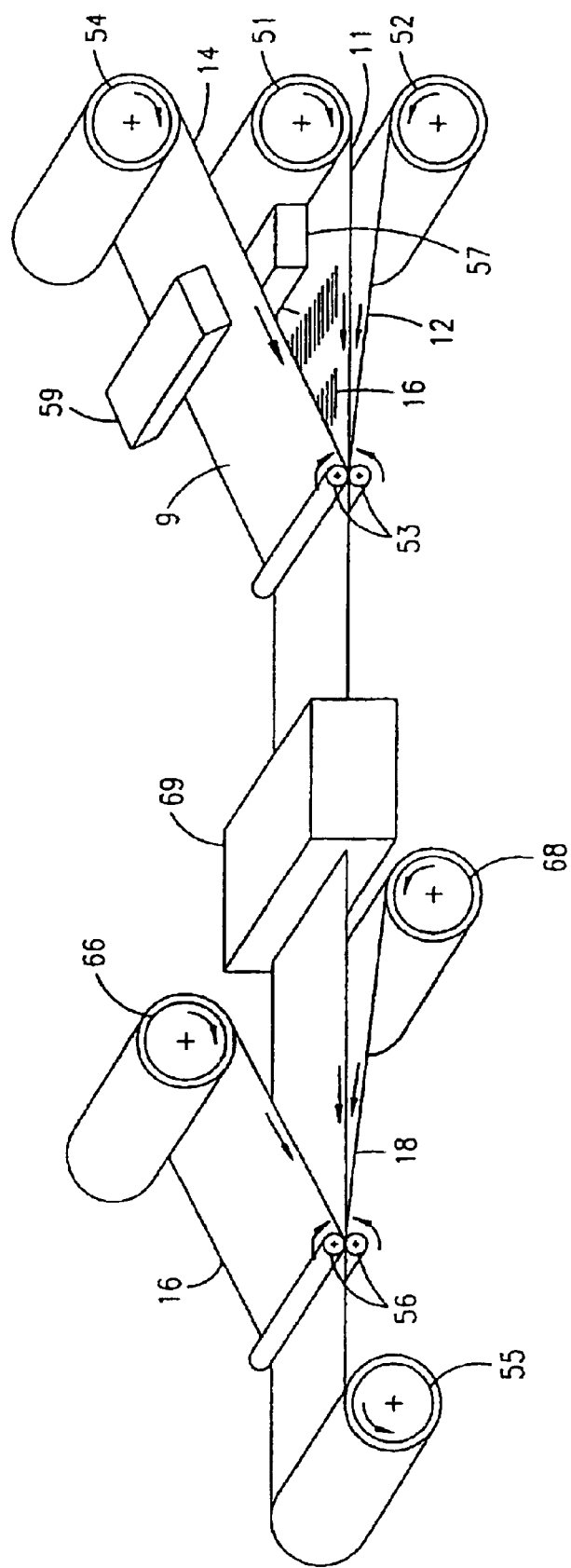
FIG. 5 is a diagrammatic sketch in a perspective view showing a method for constructing an elongate flexible film laminate having the general laminate structure shown in FIG. 1A.
Figure 6:
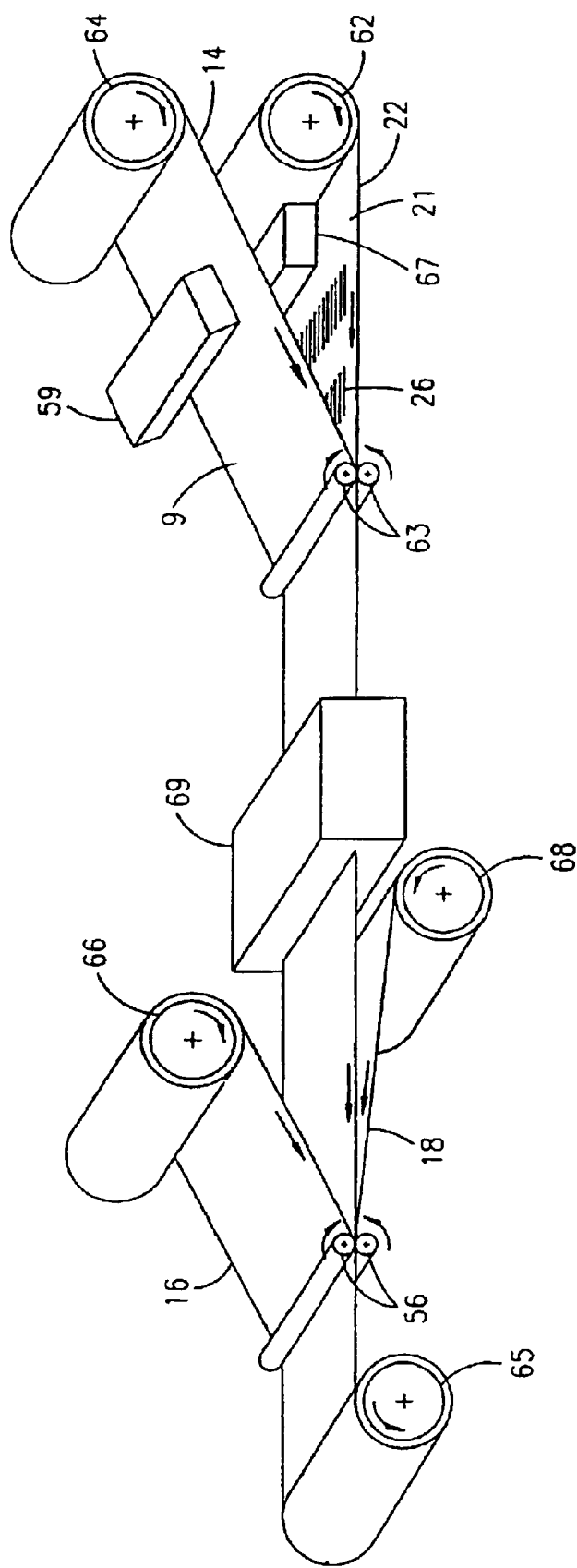
FIG. 6 is a diagrammatic sketch in a side view showing a method for constructing an elongate flexible film laminate having the general laminate structure shown in FIG. 2A.

FIGS. 5 and 6 are sketches showing in general outline schemes for constructing the laminate embodiments of FIGS. 1A and 2A. Referring now to FIG. 5, there are shown rollers 51, 52, and 54, carrying film materials to serve as, respectively, a spacing lamina 11, a base lamina 12, and a cover lamina 14. Slits 16 may be cut through spacing lamina 11 before it is rolled onto roller 51, so that the spacing lamina comes off roller 51 with the configuration of the microchannel structures already in place; or, as illustrated in FIG. 5, a cutting tool 57 may operate to cut the slits in the predetermined pattern as spacing lamina 11 is drawn from roller 51. Similarly, access openings or reservoirs 9 can be formed by perforating base lamina 12 or (as in FIG. 5) cover lamina 14 before it is stored on roller 54, so that during assembly the cover lamina comes off roller 54 with the perforations already in place; or, as illustrated in FIG. 5, a cutting tool 59 may operate to cut the predetermined pattern of perforations as cover lamina 14 is drawn from roller 54. In either method, preferred tools for cutting slits and perforations include lasers (laser cutting or laser ablation) and die cutting, for example.

Laminae 11, 12, and 14 are apposed by drawing them between rollers 53. As will be appreciated, it is essential that the perforated enclosing lamina be appropriately aligned with the spacing lamina during the lamination process, so that the perforations will be suitably aligned with the microchannels in the assembled device. Any registration technique may be used to ensure proper alignment in the longitudinal direction. Preferably, sprocket holes can be cut in one or both margins of the laminae, and the respective sprocket holes can be aligned on a sprocket. It can be suitable to provide a sprocket drive at the rollers 53, for example.

As noted generally above, certain of the components of the analytic process to be carried out in the device (buffer or solvent, separation media, etc.) can be loaded into portions of the microchannel structure before use. Particularly, it may be desirable to load certain of the constituents before enclosing the microchannels. This may be true, for example, if one or more constituents has a high viscosity at ambient temperatures, as may be true of certain electrophoretic separation media. Accordingly, as illustrated in FIG. 5, the assembled laminate formed of the spacing layer 11 enclosed by base layer 12 and cover layer 14 is drawn through a filling workstation 69, by conventional tractor means, where the selected components are injected or drawn by suction into the appropriate microchannels by way of the access perforations.

And, as noted above, where one or more components are provided on board the device, it maybe desirable to seal one or both surfaces of the device with release liners. Accordingly it is optional, as shown in FIG. 5, as the assembled and filled laminate is drawn toward takeup roller 55, to draw release liners 16 and 18 from rollers 66, 68 and between rollers 56, to appose the release liners onto the surfaces of the enclosing laminae 12 and 14. Alternatively, where the nonperforated enclosing layer is impermeable to the contents of the assembled and filled microchannel laminate of spacing layer 11 and enclosing layers 12, 14, sufficient protection of the contents can be provided by the contact of the nonperforated surface and the perforated surface when the device is rolled onto takeup roller 55, on which the device can be stored for use.

Similarly, referring now to FIG. 6, there are shown rollers 64, 62, carrying film materials to serve as, respectively, a cover lamina 14 and a base lamina 22. Channels or trenches 26 may be formed in surface 21 of base lamina 22 before it is rolled onto roller 62, so that the base lamina comes off roller 62 with the configuration of the microchannels already in place; or, as illustrated in FIG. 6, a cutting tool (or other means, as described in more detail below with reference to FIGS. 7 through 9) 67 may operate to form the trenches or channels in the predetermined pattern as base lamina 22 is drawn from roller 62. Suitable cutting techniques employ, for example, controlled laser ablation, using equipment and techniques well known in the laser micromachining industry. Suitable laser micromachining systems and protocols for their use are available from, for example, Resonetics, Nashua, N.H.

Other means for forming channels, cavities or trenches include but are not limited to heat embossing, hot embossing, ultraviolet embossing, ultraviolet curing of a liquid substance, patterning a thin film which extruding or hot stamping a surface of a film layer prior to lamination. Known micromachining techniques including. e.g., photolithographic techniques, may also be employed in forming the microstructures in the film surfaces. Alternative methods also include ultrasonic forming, pressure forming and thermal forming, vacuum forming, blow molding, stretch molding, insert molding, injection molding, extrusion casting, compression molding, encapsulation processes, thermoforming and digital printing, any of which may be employed in a continuous-form process according to the invention. Any suitable techniques such as are known in the plastics micromachining art may be employed.

Similarly, access openings or reservoirs 9 can be formed by perforating cover lamina 14 before it is stored on roller 64, so that during assembly the cover lamina comes off roller 64 with the perforations already in place; or, as illustrated in FIG. 6, a cutting tool 59 may operate to cut the predetermined pattern of perforations as cover lamina 14 is drawn from roller 64. In either method, preferred tools for perforating the cover lamina include lasers and die cutters, for example, as described above with reference to FIG. 5, for example.

Laminae 14 and 22 are apposed by drawing them between rollers 63, and properly aligned as described above with reference to FIG. 5.

Here, as in the embodiment of FIG. 5, the assembled device can be provided with one or more of the analytical components on board. Components can be loaded into the assembled device by drawing the assembled laminate formed of the base layer 22 and the cover layer 14 through a filling workstation 69, as described above with reference to FIG. 5. And, optionally where desired, as the assembled and filled laminate is drawn toward takeup roller 65, release liners 16 and 18 may be drawn from rollers 66, 68, and between rollers 56, to appose the release liners onto the surfaces of the laminate for protection.

In some embodiments according to the invention, the reservoir and microchannel are formed in the base lamina, and the flexible circuit laminate forms a cover lamina. In one approach, illustrated in FIGS. 7a and 7b, the flexible circuit laminate (that is, the cover lamina) is made up of two layers, namely, a seal layer and a back layer. In this embodiment part of the conductive trace is formed on the back surface of the seal layer, and part is formed in the front surface of the back layer. In another approach, illustrated in FIGS. 8a and 8b, the flexible circuit layer is made up of three layers, namely a seal layer, which carries no conductive trace, and two circuit layers, each carrying a conductive trace. One of these circuit layers is a back layer, and the other is laminated between the back layer and the seal layer.

Figure 7A:
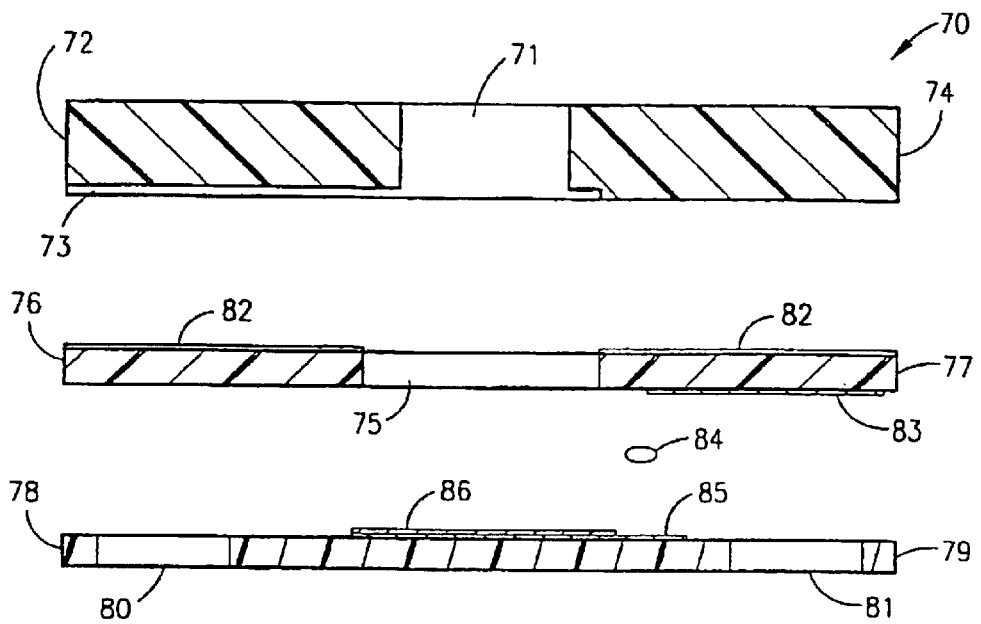
FIGS. 7a, b are diagrammatic sketches in sectional view showing details of an embodiment of a device according to the invention made using a flexible circuit lamina.
Figure 7B:
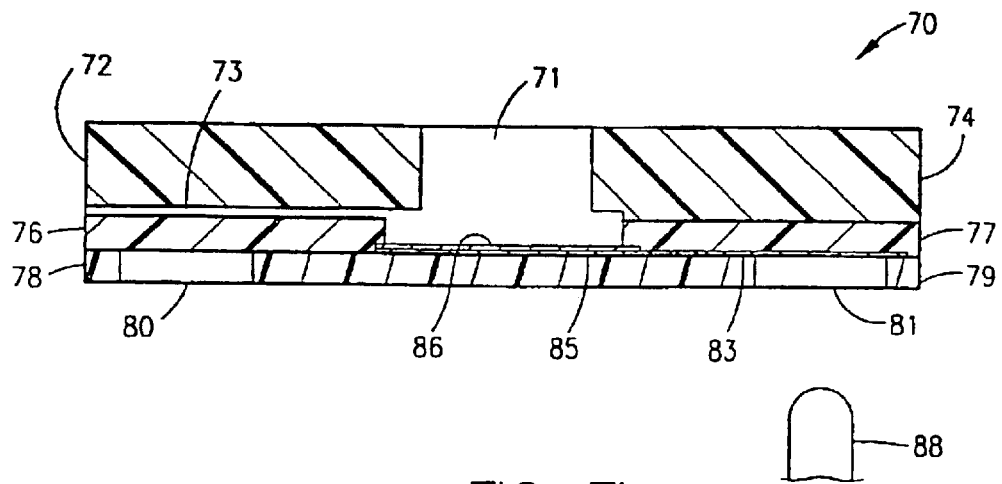

Referring now to FIGS. 7a, 7b, there is shown generally at 70 a portion of a microstructure device according to the invention, in transverse section thru a reservoir and microchannel and associated circuitry. The device consists of a base lamina 72, constructed of a generally planar plastic material 74, a seal layer 76, formed of a low fluorescence polymer film 77, and a back layer 78, formed of a plastic film 79. Formed in the polymer base lamina 74 are reservoir or well 71 and microchannel 73 of a microstructure. An opening 75 is formed through the seal layer film 77 in register with the reservoir 71. A front surface of seal layer film 77 is provided with an adhesive 82, which will serve to seal the seal layer and the base layer together when assembled, as shown in FIG. 7b. A rear surface of the seal layer is provided with contact conductive trace portion or trace 83 of the circuitry. A detection clearance opening 80 is formed through back layer film 79 in register with a detection zone of the microchannel 73, and a contact opening 81 is formed through back layer film 79 in register with the contact conductive trace portion 83. A front surface of the back layer film 79 is provided with a second conductive trace 85, having one region in register with a region of the contact conductive trace 83 and another region in contact with a carbon electrode or electrode portion 86, which in turn is in register with the reservoir 71. A conductive adhesive 84 provides for good conductive adhesion between conductive traces 83, 85, when assembled, as shown in FIG. 7b. It should be appreciated that layers 72, 76 and 78 can optionally be sandwiched between top and bottom release layers (not shown) similar to layers or liners 16,18 discussed above. The top release layer can seal reservoir 71. The bottom release layer can be provided with openings in registration with openings 80,81 in the back layer 78. Referring now to FIG. 7b, an electrical contact or electrode probe 88 in the analytical instrument contacts the conductive trace portion or contact portion of the circuitry by way of the contact opening in the back layer, and a photodetector (not shown in the Figs.) detects the signal in the microchannel through the low fluorescence film of the seal layer by way of the detection opening 80 in the back layer. Conductive traces 83,85 and carbon electrode 86 are included in the electrical means of microstructure device 70.

Where laser-induced fluorescence detection is employed, preferred low fluorescence materials have sufficiently low fluorescence at the illuminating and back scattering wavelengths that the presence of the film in the optical path does not significantly reduce detection. Examples of suitable such materials include impact modified acrylic (e.g., Rohm film 99530), polyethylene terephthalate ("PET"), polyolefins (e.g., Zeonex), and acetates. The adhesive also preferably has low fluorescence characteristics, and preferably has surface characteristics similar to those of the walls of the channel, inasmuch as the adhesive will form one inner surface of the microchannel when assembled, and differences could a adversely affect electroflow in the channel. Suitable such adhesives include organic based acrylic adhesives.

Figure 8A:
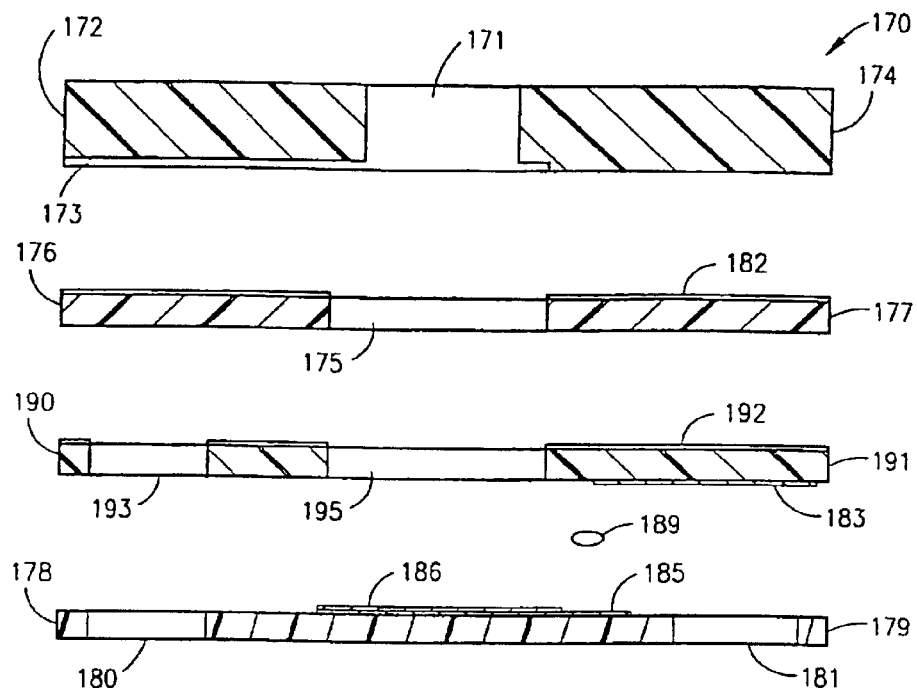
FIGS. 8a, b are diagrammatic sketches as in FIGS. 7a, b showing details of an alternative embodiment of a device according to the invention made using a flexible circuit lamina.
Figure 8B:
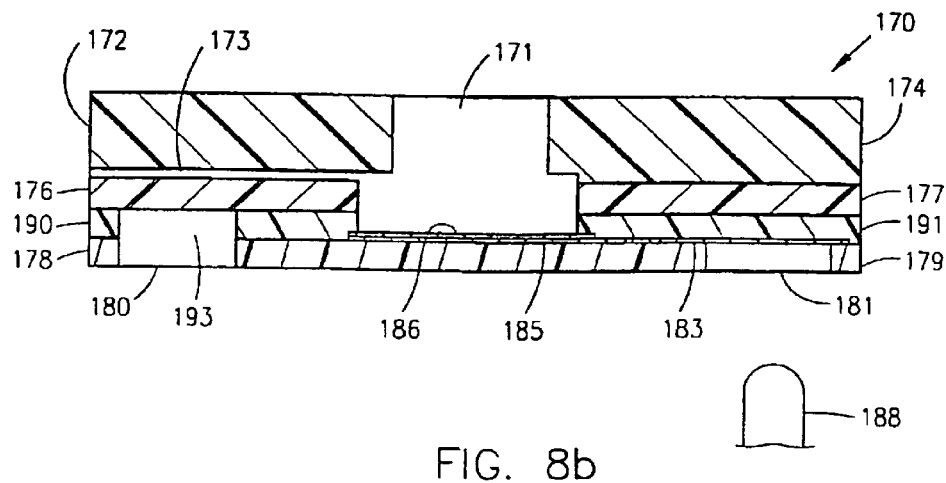

Referring now to FIGS. 8a, 8b, there is shown generally at 170 a portion of an alternative embodiment of a microstructure device according to the invention, in transverse section thru a reservoir and microchannel and associated circuitry. The device consists of a base lamina 172, constructed of a generally planar plastic material 174, a seal layer 176, formed of a low fluorescence polymer film 177, a back circuit layer 178, formed of a plastic film 179, and an intermediate circuit layer 190, formed of a polymer film 191. Formed in the polymer base lamina 174 are reservoir or well 171 and microchannel 173 of a microstructure. An opening 175 is formed through the seal layer film 177 in register with the reservoir 171. A front surface of seal layer film 177 is provided with an adhesive 182, which will serve to seal the seal layer and the base layer together when assembled, as shown in FIG. 8b. A back surface of the intermediate circuit layer film 191 is provided with contact conductive trace portion or trace 183 of the circuitry, and a front surface of the intermediate circuit layer film 191 is provided with an adhesive 192, which will serve to seal the intermediate circuit layer film 191 to the seal layer 177 when assembled, as shown in FIG. 8b. An opening 195 is formed through the intermediate circuit layer 190, in register with the opening 175 in the seal layer and with the reservoir 171. An intermediate detection clearance opening 193 is formed through intermediate circuit layer film 191 in register with a detection zone of the microchannel 173. A detection clearance opening 180 is formed through back layer film 179 in register with a detection zone of the microchannel 173, and a contact opening 181 is formed through back layer film 179 in register with the contact conductive trace portion 183. A front surface of the back layer film 179 is provided with a second conductive trace 185, having one region in register with a region of the contact conductive trace 183 and another region in contact with a carbon electrode or electrode portion 186, which in turn is in register with the reservoir 171. A conductive adhesive 189 provides for good conductive adhesion between conductive traces 183, 185, when assembled, as shown in FIG. 8b. It should be appreciated that layers 172, 176, 178 and 190 can optionally be sandwiched between top and bottom release layers (not shown) similar to layers or liners 16, 18 discussed above. The top release layer can seal reservoir 171. The bottom release layer can be provided with openings in registration with openings 180,181 in the back layer 178. Referring now to FIG. 8b, an electrical contact or electrode probe 188 in the analytical instrument contacts the contact conductive trace portion or contact portion of the circuitry by way of the contact opening in the back layer, and a photodetector (not shown in the Figs.) detects the signal in the microchannel through the low fluorescence film of the seal layer by way of the detection opening 180 in the back layer. Conductive traces 183,185 and carbon electrode 186 are included in the electrical means of microstructure device 170. In this embodiment, the flexible circuit laminate (made up of the two circuit layers) can be constructed separately from the base layer and seal layer, because the seal layer does not include any circuitry. Moreover, because in this embodiment there need not be a good seal between the flexible circuit laminate and the microchannels in the base layer, it is not necessary that the flexible circuit laminate have a surface that conforms precisely with the surface of the base layer.

An embodiment of a microstructure array device according to the invention, provided with flexible circuitry constructed generally as described above, is shown in FIGS. 11a, 11b, 11c. In this example, the elongate flexible film laminate contains a plurality of microstructure arrays arranged serially lengthwise along the laminate. Each microstructure array in this illustrative embodiment includes four microstructures, each configured to carry out an analytic process.

Figure 11A:
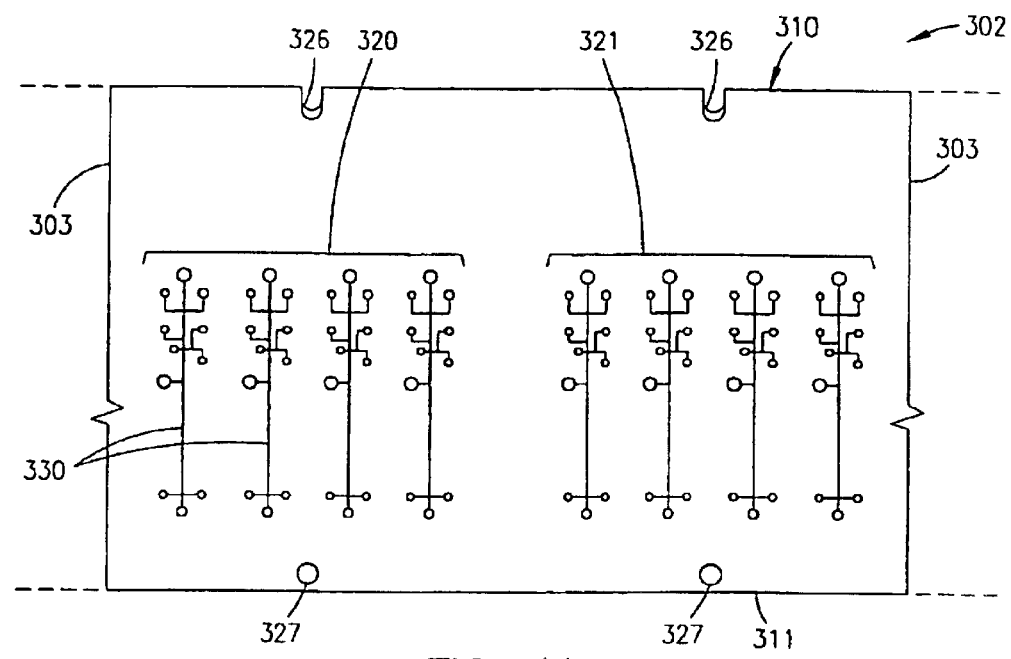
FIG. 11a is a diagrammatic sketch of a portion of the length of an embodiment of a base lamina of a continuous form microstructure device of the invention, showing two in a series of microchannel arrays. Each microchannel array includes four microstructures each configured to carry out a receptor binding assay, as described with reference to FIG. 9.

Referring now to FIG. 11a, there is shown a short segment of an elongate flexible film base lamina or microstructure device 302 which extends lengthwise beyond the range of the drawing, as indicated by broken lines extending from the edges 310, 311 of the short segment. The short segment shown, which is limited by lines 303, includes two successive microchannel arrays 320, 321. Each of the microchannel arrays 320, 321 in this illustration contains four microstructures, two of which are indicated for example at 330, each configured and designed for carrying out a receptor binding assay, as described in detail in Example 1 below, with reference to FIG. 9. Near the edge 310 and associated with each array is a pin registration slot 326, and near the edge 311 and associated with each array is a pin registration hole 327.

Figure 11B:
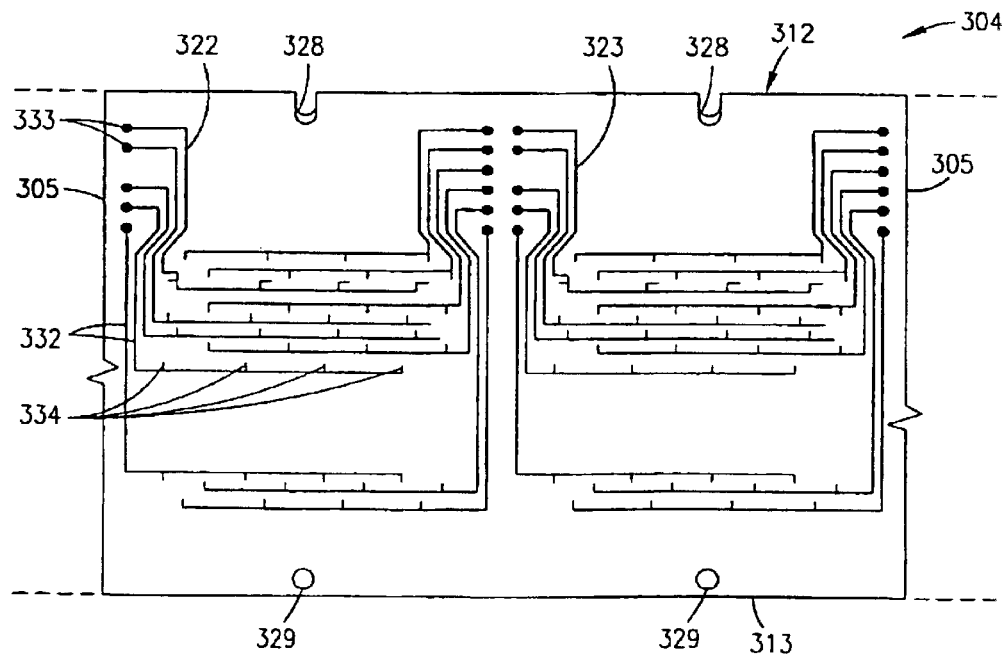

FIG. 11b shows a corresponding flexible circuit laminate or microstructure device 304, which also extends beyond the range of the drawing, as indicated by broken lines extending from the edges 312, 313. The short segment shown, which is limited by lines 305, includes two circuit layouts 322, 323, each configured to serve a microchannel array 320, 321 (shown in FIG. 11a) in the assembled device. The flexible circuit laminate can be constructed generally as described above with reference to FIGS. 8a, 8b, for example. The circuits consist of conductive traces (two are shown at 332, for example) each connecting a contact terminal (two are shown at 333, for example) to four electrodes (334, for example) each located at a point corresponding to the positions of a reservoir in one of the four microstructures in the array.

Figure 11C:
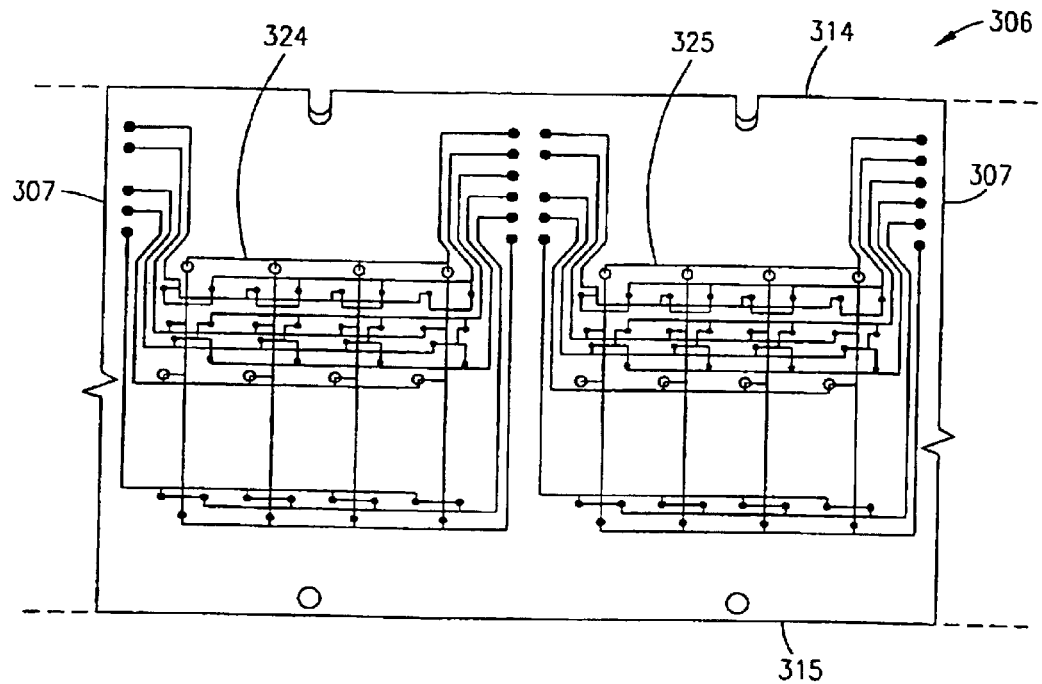

Near the edges 312, 313, the flexible circuit laminate 304 is provided with pin registration slots 328 and holes 329, associated with the circuit layouts such that when the base lamina and the flexible circuit laminate are assembled and the respective slots and holes are aligned, precise superposition of the electrodes over the respective reservoirs is ensured. Referring now to FIG. 11c, there is shown generally at 306 a short segment of an embodiment of an assembled continuous form microstructure device of the invention, made by laminating the base lamina of FIG. 11a and the flexible circuit laminate of FIG. 11b. As in FIGS. 11a, 11b, the device extends beyond the range of the drawing, as indicted by broken lines extending from edges 314, 315; and the short segment shown, which is limited by lines 307, includes two microstructure arrays 324, 325, each capable of carrying out four receptor binding assays under the control of the associated circuit layout.

The laminate is constructed, as described above, so that the contact terminals are accessible by contact points through contact holes in the cover film. Accordingly, as the laminate is carried through the analytical device, sets of contact points are brought into contact with the corresponding sets of contact terminals on the laminate device. The contact points, in turn, are connected to a source of electrical power, which is provided with controls to change the voltages at the electrodes in a pattern determined according to the sequence of electroflow manipulations to be carried out in the microstructures over the course of the assay.

EXAMPLES

Example 1

Receptor Binding Assay

This Example illustrates a microstructure configuration and method for carrying out a membrane-receptor competitive binding assay according to the invention.

In this Example, cell membrane receptors are attached to solid-phase capture media for facilitating the use of protein receptors in a microfluidic-based assay. Solid-phase attachment of the receptor can be achieved in one of several ways, including, e.g., the use of activated paramagnetic beads or other synthetic particles.

This assay is particularly applicable for receptors belonging to the seven transmembrane family or similar proteins wherein the sequence of amino acids traverses the membrane multiple times. These targets, e.g., the G-protein coupled receptor (or GPCR), are more likely than others to require the physical environment of the membrane lipid bilayer for physiologically relevant interactions. The dopamine receptor is a specific example of the broader class of GPCR proteins.

A membrane-receptor competitive-binding assay in regard to the above is provided. The non-isotopic assay comprises of two binding events. The primary receptor-ligand affinity reaction can be written generally as:

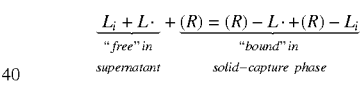

where the library test compound $L_i$ and labeled ligand L• compete for receptor binding sites (R) on the immobilized cell membrane protein. Once the unbound ligand L•, which remains "free" in the supernatant, is removed, then the bound ligand, which is complexed with the immobilized receptor beads, can be detected using a fluorophore-labeled secondary binding protein. If a biotinylated ligand is employed in the primary bioaffinity reaction, then solid-phase fluorescence detection is possible based on the following binding reaction:

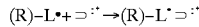

where ⊃∶* represents, for example, an avidin-fluorescein conjugate, as the other member of the secondary specific binding pair. Other protocols based on methods of the invention are also possible. For example, a detection scheme may be employed based upon depletion monitoring of the labeled ligand L˙.

Figure 9:
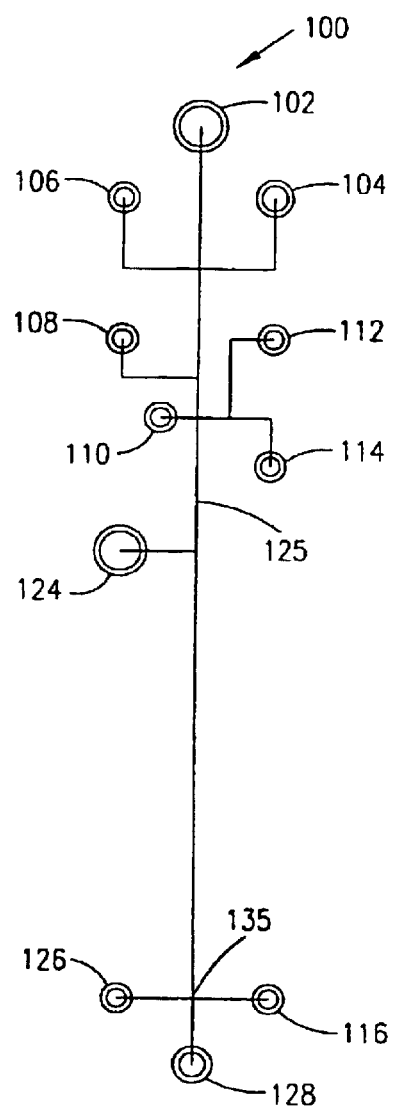
FIG. 9 is a diagrammatic sketch showing a microstructure configuration that can be constructed in a continuous form laminate device of the invention, suitable for carrying out a receptor binding assay.

Such an assay can be carried out using a microfluidic assay device according to the invention, configured, in one embodiment, as shown generally at 100 in FIG. 9. Referring now to FIG. 9, there is shown an assay laminate or microstructure device 100, on which the microstructure is formed. The microstructure includes chambers and reservoirs that are connected in fluid communication by microchannels.

Particularly, device or card 100 includes a zone 125 in which incubation is carried out and separation and detection can be carried out; a secondary capture and detection zone 135; a number of inlet reservoirs: reservoir 102, which serves as a supply of buffer solution; a reservoir 104, serving as a source of library test compound ligand i; reservoir 106, serving as a source of a biotin-labeled ligand conjugate, or biotinyated tracer; reservoir 108, serving as a source of fluorophore-labeled secondary binding protein, or fluorescent tracer; reservoir 110, serving as a source of bead-immobilized, membrane-bound receptor; wash buffer reservoir 112; reservoir 114, serving as a source of an agent that cleaves the fluorophore tag from the fluorescent tracer conjugate; and capture compound source reservoir 116; and a number of outlet reservoirs: reservoir 124, to receive waste from the binding assay from the fluorescent tracer conjugate; reservoir 126, to receive waste capture compound; and reservoir 128, to receive waste supernatant from binding.

Each reservoir can be provided with an electrode that is connected to a source of electrical power, and potential differences among the various electrodes can be controlled and manipulated to selectively induce electrokinetic transport to and from the reservoirs and within the microchannels and chambers.

In preparation for the assay, the receptors are immobilized as follows. Magnetic latex beads, preactivated to covalently bind protein, are bound to a lectin such as wheat germ agglutinin (WGA). Upon completion of this step, unreacted or exposed bead surface is blocked from nonspecific interactions by incubation with a saturating concentration of carrier protein such as bovine serum albumin or gelatin. Then the WGA coated beads are co-incubated with coil membranes having on them the receptor of interest. This interaction may conclude with an additional blocking step, to remove or inactivate potential sites of nonspecific binding.

With reference again to FIG. 9, the bioanalytical assay proceeds on the microfluidic device 100 as follows.

1. A fixed quantity of receptor-bound beads are introduced into reservoir 110. Then the beads are transferred, by means of an applied magnetic field or electrokinetic flow, to chamber 125 by way of a microchannel in fluid communication with the reservoir and the chamber. In this particular assay protocol, the beads are held in chamber 125 for the duration of the procedure.

2. Next, the compound $L_i$ to be tested for binding ability is moved from reservoir 104 by electrokinetic means through communicating microchannels into chamber 125; and either concurrently therewith or thereafter, a standard compound L• of known binding properties, is moved from reservoir 106 into chamber 125. This latter compound L• contains a member of a directly or indirectly detectable signal-producing system, for example, covalently attached biotin.

3. After an appropriate series of electrokinetically driven wash steps using wash buffer moved from reservoir 112, a determination is made for the amount of unknown compound $L_i$ that binds by determining the degree to which it displaces the standard compound L•. This is measured by introducing the secondary fluoro-labeled binding protein into reaction chamber 125 from reservoir 108 and allowing the complex of compound and receptor, (R)-L•, to react with the streptavidin which binds biotin with high affinity. The amount of streptavidin captured is monitored directly when a fluorescent label is associated with the streptavidin.

4. In some embodiments of the assay in this Example, the amount of fluorescent label associated with the membranes is determined by direct measurement in the capture zone. In other forms of the assay, the fluorescent label may be attached via a disulfide bond (denoted by """). This bond is readily cleaved under reducing conditions. Accordingly, dithiothreitol, or beta mercaptoethanol stored in reservoir 114 may be used to release the fluorescent label (denoted by "*").

5. The fluorescent labeled species can then be separated from other reactants by electrokinetic or hydrodynamic enhanced electroseparation techniques. To facilitate detection, the magnetic beads may be immobilized at a site along the capillary path 125 by application of a magnetic field. The fluorescent label may be detected at that site or at a site 135 downstream therefrom. The fluorescent label may be detected in the fluorescent labeled species, or the fluorescent label may be cleaved and detected separately.

Example 2

Enzyme Assay.

This Example illustrates a microstructure configuration and method for carrying out an enzyme assay according to the invention, which can be particularly useful in high-throughput pharmaceutical drug discovery and screening applications.

In this Example, an enzyme, a labeled substrate, and an inhibitor are mixed and allowed to incubate, and then the labeled product of the enzymatic reaction and the labeled unreacted substrate are separated electrophoretically and each is quantitatively determined by detection of the label.

Figure 10:
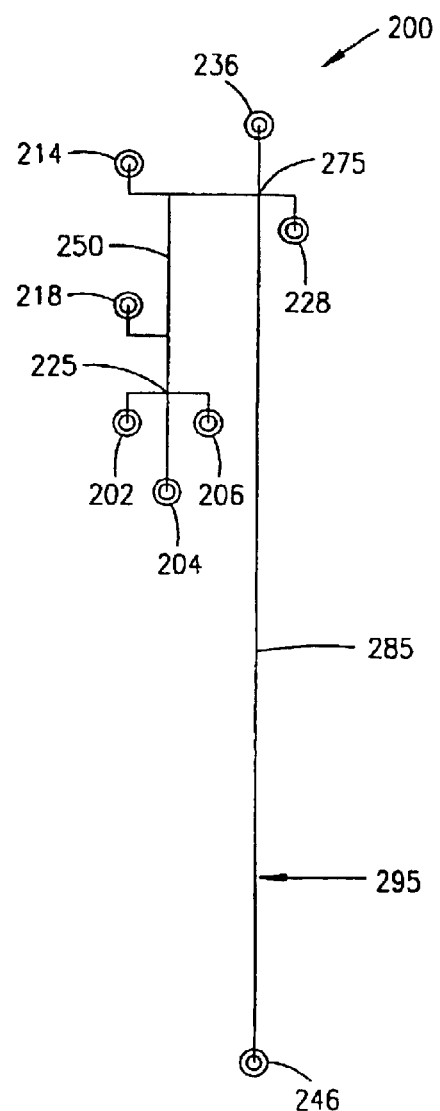
FIG. 10 is a diagrammatic sketch showing a microstructure configuration that can be constructed in a continuous form laminate device of the invention, suitable for carrying out an enzyme assay.

Such an assay can be carried out using a microfluidic assay device according to the invention, configured, in one embodiment, as shown generally at 200 in FIG. 10. Referring now to FIG. 10, there is shown an assay laminate or microstructure device 200 on which the microstructure is formed. The microstructure includes an incubation chamber 250, an injection cross 275, an electrophoretic separation channel 285, and detection zone 295, connected in fluid communication by microchannels with a number of reservoirs, including inlet reservoirs: reservoir 202, for supply of enzyme, which is usually a kinase, and containing ATP and $Mg^{2+}$; reservoir 204, for supply of labeled substrate S*, which is usually a fluorophore-labeled peptide; reservoir 206, for supply of enzyme inhibitor; reservoir 218, serving as a supply of assay buffer, and employed to electrokinetically transport the product mixture stream to an outlet reservoir 228; and reservoir 236, serving as a supply of running buffer, and employed to electrokinetically transport a metered plug of the product mixture into the separation channel 285 and the outlet reservoir 246; and a number of outlet reservoirs: reservoir 214, to receive a mixture of excess enzyme, substrate, and inhibitor; reservoir 228, for receiving product mixture stream; and reservoir 246, for receiving detection product waste.

Each reservoir can be provided with an electrode that is connected to a source of electrical power, and potential differences among the various electrodes can be controlled and manipulated to selectively induce electrokinetic transport to and from the reservoirs and within the microchannels and chambers.

In some particularly useful embodiments, the enzyme inhibitor is a pharmaceutical drug candidate, and the assay is carried out to determine the effectiveness of the candidate as an inhibitor for the particular enzyme. Usually the enzyme is a tyrosine specific protein kinase such as, for example, Src kinase; and usually the labeled substrate is a fluorophore-labeled peptide such as, for example, cdc-2 peptide.

The enzyme assay proceeds on the microfluidic device 200 as follows.

1. Mixing. Reagents are moved electrokinetically from inlet reservoirs 202 (enzyme), 204 (substrate), and 206 (inhibitor) toward outlet reservoir 214. Mixing of the reagents occurs in mixing cross 225 and in incubation chamber 250.

2. Incubation. The fluid flow is halted electrokinetically by adjustment of the various potentials in order to let enzyme, substrate and inhibitor incubate in incubation chamber 225.

3. Injection. A continuous stream of the product and excess reagent mixture are moved out from the incubation chamber 250 and into the outlet reservoir 228, using the inlet reservoir 218 as the source of the assay buffer to electrokinetically drive the fluid transport.

4. Separation. A plug of the product mixture is electrokinetically injected from the injection cross 275 into the electrophoretic separation channel 285 and then into waste outlet reservoir 246 using inlet reservoir 236 as the source of the running buffer to electrokinetically drive the fluid transport. As a result of mobility shift produced by conversion of labeled substrate S* to product P*, S* and P* are separated electrophoretically as they are electrokinetically transported in separation channel 285. Laser-induced fluorescence monitoring of the labeled substrate and product is achieved in the detection zone 295. Because the mobility shift is usually expected to result from differences in charge/mass ratio between S* and P*, a gel matrix is usually not required to achieve separation.

As the Examples illustrate, the invention is useful in a wide variety of applications involving techniques and protocols in fields of, for example, cell biology, molecular biology, HLA tissue typing, and microbiology. More specifically, for example, the invention can be applied to techniques for immunodiagnostics, DNA purification from whole blood and other samples, mRNA isolation, solid phase cDNA synthesis, receptor-binding assays, drug screening and discovery, and cell isolation.

Other embodiments are within the following claims. For example, assay devices other than microchannel devices can be adapted in a continuous form assay array format generally as described herein, to provide high throughput systems For example, the fluids (reagents, samples, etc.) employed in the assay can be mixed and measured in wells (that is, in cavities) constructed in an elongate laminate device, and not necessarily directed by microfluidic manipulation.

And, for example, microstructures or arrays of microstructures may be formed in more than one lamina in the laminated device according to the invention, so that microstructures in one lamina are superimposed over microstructures in another. The superimposed microstructures may, for example, carry out different but related processes or process steps in a fluidic process and, by providing for fluid communication between the laminae, fluids may be transported from one microstructure to another in the course of the process. This permits related processes to be carried out in close proximity under similar conditions, and without a need for transfer of products or byproducts or intermediates from one reaction container (or from one microstructure) to another. Fluid communication between laminae can be provided by, for example, simply perforating the layer that separates the microstructures, and control of the flow through such a perforation can be done, preferably in a valveless fashion, by any of the various means employed for moving fluids within the microstructure of a lamina.

As will be appreciated, although the device according to the invention is described above as being used in continuous processing form, individual microstructures or arrays in an elongate laminate made as described above can be separated one from another, and used as discrete devices in "card" form, each containing a microstructure or an array of microstructures. As may be desired, the elongate laminate may, where such use is contemplated, be made easily separable between successive microstructures or arrays, for example by perforating or scoring the laminate, or cutting the laminate partway through. Use of the laminate in this way preserves the advantages of continuous form in the manufacture of the device, and replaces advantages of using the device in continuous form with advantages of handling discrete card-form microfluidics devices.

Approaches to aligning the laminae during manufacture other than through holes or notches can be used, for example, techniques employing optical, electrical, and ultrasonic alignment, or employing other mechanical means such as ratchets.

It should be appreciated that any of the microstructure devices described above, including those manufactured in accordance with the processes shown in FIGS. 5 and 6 and described above, can be cut or diced into a plurality of discrete card-like microstructure devices, each having a plurality and more specifically an array of discrete microstructures formed therein. Such card-like devices can be used for any of the uses described above. Although such card-like devices can be of any suitable size, in one preferred embodiment such devices can be sized on the order of a credit card.

Figure 12:
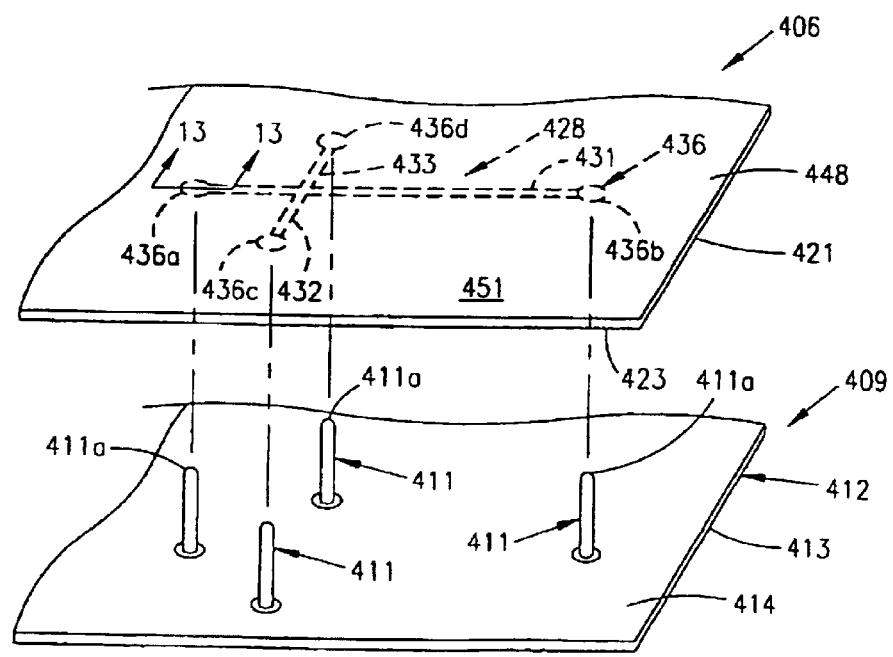
FIG. 12 is an isometric view of a laminate microstructure device of the present invention and a contact probe assembly for use therewith.
Figure 13:
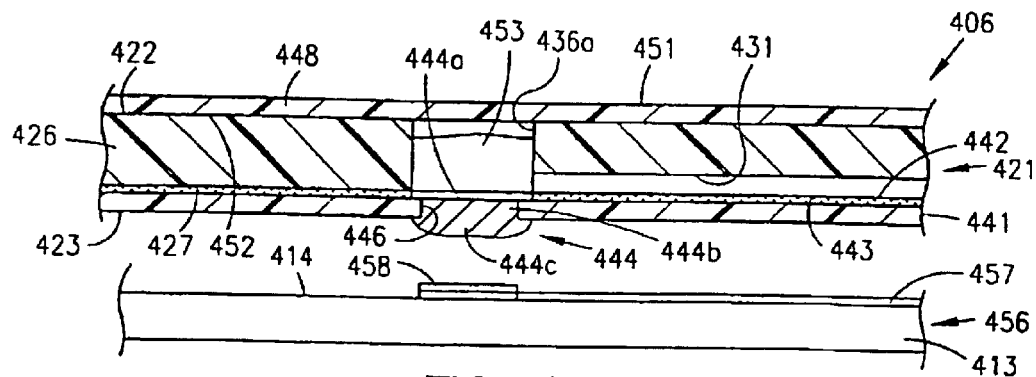
FIG. 13 is a cross-sectional view of the laminate microstructure device of FIG. 12 taken along the line 13—13 of FIG. 12 with another embodiment of a contact probe assembly for use therewith.

Another embodiment of the microstructure device of the present invention is shown in FIGS. 12 and 13. Microstructure device 406 therein is formed from a laminated structure having a plurality of separate layers or laminae joined together. Microstructure device 406 is preferably a discrete or card-like device, but can also be an elongate flexible device suitable for storage on a reel. The microstructure device 406 is for use with a contact probe assembly 409 having a plurality of contact probes 411 arranged in a predetermined pattern on any suitable support structure 412, shown in FIG. 12 as being a body 412 having a planar surface 413. The elongate contact or electrode probes 411 are made from any suitable conductive metal and in the embodiment of the contact probe assembly 409 shown in FIG. 12 are needle-like in conformation and preferably compliant vertically to facilitate electrical coupling with microstructure device 406. Each of the probes 411 is formed with a rounded end 411a. The probes 411 extend perpendicularly from surface 413 in a predetermined pattern. Although probes 411 are shown as rigidly mounted on support structure 412 so as to remain static during operation, the probes can be mounted on the support structure 412 for retraction and extension from a plurality of bores that open onto surface 414. Separate electrical leads (not shown) are carried by support structure 412 for connection to each of the contact probes 411. Such leads are, in turn, connected serially or separately to a controller (not shown) which provides appropriate electrical signals, preferably in the form of voltage potentials, to the probes 411.

Microstructure device 406 has a thickness ranging from approximately 100 microns to three millimeters and preferably ranging from approximately 150 microns to one millimeter. The microstructure device 406 includes a laminate structure 421 having first and second spaced-apart planar surfaces 422 and 423 which form two exterior surfaces of the laminate structure 421 (see FIG. 13). A first layer or lamina 426 is included within laminate structure 421. The first lamina or card body 426 is made from any suitable nonconductive material such as plastic and can be relatively rigid or flexible depending on the particular use of microstructure device 406. In one embodiment of a card-like device 406, the first lamina 426 is relatively rigid to provide rigidity to the device 406. Alternatively, other layers in the laminate structure 421 can be relatively rigid, in addition to or instead of a rigid lamina 426, if a rigid microstructure device 406 is desired First lamina 426 has a first planar surface in the form of first or top surface 422 and a second planar surface 427 spaced apart from the top surface 422 and interior of the laminate structure 421.

The laminate structure is provided with at least one microstructure 428 of capillary dimensions, and preferably a plurality of microstructures 428, formed therein and extending in a direction parallel to the parallel surfaces 422 and 427 of the first lamina 426. For simplicity, only one microstructure 428 is shown in FIG. 12. More specifically, each of the microstructures 428 is formed in first lamina 426 and extends through one of the planar surfaces 422, 427 of the first lamina. As shown in FIG. 13, microstructures 428 open onto second or lower surface 427 of the first lamina 426. Each microstructure 428, as shown in FIG. 12, preferably includes at least first and second microchannels 431 and 432 which meet at an intersection 433. Laminate structure 421 is provided with at least one and as shown a plurality of holes or wells 436 in fluid communication with each microstructure 428. In one preferred embodiment of microstructure device 406, first and second wells 436a and 436b are provided at the first and second end portions of first microchannel 431 and third and fourth wells 436c and 437d are provided at the first and second ends of second microchannel 432. It should be appreciated that the wells 436 can be provided at other locations within microstructure 428 and be within the scope of the present invention. Each of the wells 436, as shown with respect to first well 436a in FIG. 13, is adapted to receive a fluid and consists of a bore extending between surfaces 422, 427 of first lamina 426 and is accessible from the top surface 422 of the laminate structure 421. Wells 436 can be sized to receive approximately one microliter of such fluid.

Laminate structure 421 includes a second layer or lamina 441 made from any suitable non-conductive material such as plastic. Second lamina or film 441 has a first planar surface 442 and a second planar surface in the form of second or bottom surface 423 which is spaced-apart from and parallel to the top surface 422. Second lamina 441 is secured to first lamina 426 by any suitable means such as an adhesive layer 443 disposed between surfaces 427 and 442. In an alternative embodiment, surfaces 427 and 442 can be diffusion bonded together and adhesive layer 443 thus eliminated.

A plurality of electrical means 444 are at least partially carried by second lamina 441. The electrical means 444 are preferably equal in number to the number of wells 436 provided in laminate structure 421 such that each of the wells 436 has a corresponding electrical means 444. Each of such electrical means 444 includes an electrode portion 444a in communication with any fluid provided in the well 436 and a contact or pad portion 444b spaced apart from electrode portion 444a and not in contact with any such fluid in well 436. An interconnect portion 444c connects the electrode portion 444a to the contact portion 444b. In the embodiment of the microstructure device shown in FIGS. 12 and 13, each electrical means 444 extends through a bore 446 between surfaces 442 and 423 of the second lamina 441 such that the electrical means resembles a circular plug or disk disposed in the second lamina 441. Bore 446 has a diameter smaller than the diameter of well 436 so as to minimize fluid contact with the material of electrode portion 444a. The electrical means 444 are each made from any suitable material such as conductive carbon ink. Conductive metals such as silver, copper, gold, platinum and palladium, other conductive inks such as metalized inks and blends of conductive materials and polymers such as conductive epoxies and conductive adhesives are also suitable materials for electrical means 444. Electrode portion 444a is disposed adjacent first or upper surface 442 of the second lamina and interconnect portion 444c is disposed in bore 446. Contact portion 444b is disposed adjacent bottom surface 423 of the second lamina 441 and underlying the electrode portion. The contact portion 444b can extend downwardly from bottom surface 423 and have a rounded end as shown in FIG. 13. The diameter of the contact portion 444b is larger than bore 446 so that a portion of the contact portion sits on the bottom surface 423 for facilitating retention of the electrical means 444 in bore 446 during engagement with contact probes 411. Electrode portion 444a and contact portion 444b are aligned with the respective well 436 and electrode portion 444a forms at least a portion of the bottom surface of such well 436.

Contact portions 444b are accessible from the exterior or bottom surface 423 of laminate structure 421 and microstructure device 406 without need of penetrating any of the layers of such structure 421 and device 406. In addition, contact portions 444b are arranged on bottom surface 423 in a pattern which corresponds to the predetermined pattern of contact probes 411. As such, the contact probes 411 can register with and simultaneously or otherwise engage respective contact portions 444b when microstructure device 406 and support structure 412 are moved relative to each other into close proximity with each other.

Microstructure device 406 can optionally include a third layer or lamina 448 made from any suitable material such as plastic. The third lamina 448 overlies each of wells 436 and is secured to laminate structure 421 by any suitable means such as heat bonding so as to suitably secure any fluid located within the wells. Alternatively, the cover lamina 448 can be removably or temporarily secured to the laminate structure 421 by an adhesive or any other suitable means to permit removal and reattachment of the cover lamina. The third lamina 448 has a first or upper planar surface 451 which serves as an exterior surface of microstructure device 406 and a second or lower planar surface 452 which is adhered to top surface 422 of laminate structure 421 by a pressure sensitive adhesive, heat bonding or any other suitable means.

In operation and use, a fluid and preferably a liquid is provided in each well 436. A fluid 453 is shown in FIG. 13 in first well 436a. Such fluids can be supplied to wells 436 during manufacture of microstructure device 406 or immediately prior to use of the device 406 and can be a single fluid or a plurality of fluids of different composition. Fluids can be sealed in the wells 436 by means of third or cover lamina 448. Cover lamina 448 permits fluids to be supplied to wells 436 during manufacture of the device 406 and stored therein during transport. Prior to use, the cover lamina 448 can be pierced if additional fluids need be added to one or more wells 436 or, if the cover lamina 448 is removable, removed for the supply of such additional fluids and optionally reattached thereafter. Cover lamina 448 advantageously inhibits evaporation of fluids contained in wells 436 and microstructures 428.

Contact portions 444b and contact probes 411 are brought into engagement to permit electrical coupling thereof. In this regard, microstructure 406 can be placed upon contact probes 411 or, alternatively, contact probes 411 brought into contact with the microstructure device 406. In either instance, contact probes 411 simultaneously engage respective contact portions 444b. A force can optionally be applied to the top surface of microstructure device 406 to enhance electrical contact between contact portions 444b and contact probes 411. A distributed force can be applied to the top surface of device 406 by means of pressurizing the top surface in a conventional manner with any suitable fluid such as air or argon gas.

Microstructure devices 406 can be used in any of the processes described or referenced above. During such processes, the fluids provided in wells 436 can be electrokinetically transported through microstructure 428 by means of voltage differentials provided between appropriate wells 436. Probes 411 provide a predetermined voltage potential to one or more electrode portions 444a when such voltage potential is supplied by the controller. The sequence and timing of such voltage potentials determine the manner in which fluids flow through microstructures 428.

It should be appreciated that all or portions of cover lamina 448 and laminate structure 421 can be made from materials which are optically transparent so as to permit optical detection of the fluids within microstructures 428 and/or wells 436. Alternatively, microstructure device 406 can be adapted for use with other conventional detection devices for determining characteristics of the fluids within microstructures 428 and/or wells 436.

Microstructure device 406 permits electrical potentials to be provided to each of the wells 436 therein without the need of contact probes 411 being inserted directly into the fluid within such wells. Instead, electrical probes 411 each engage a contact portion 444b which transmits the electrical potential of the contact probe 411 to electrode portion 444a in contact with the fluid within the well 436. Contact probes 411 are thus not contaminated with the fluid of the wells 436 and can be used in the operation of a second microstructure 406 without fear of mixing the fluids from the first microstructure device with the fluids in the second microstructure device. As can be seen, contact probes 411 can be repeatedly used in a process which sequentially analyzes and/or detects characteristics of fluids supplied to a plurality of microstructure devices 406. The close proximity of the electrode portions 444a to the contact portions 444b inhibit current losses in the electrical means 444.

Microstructure device 406 can be used in the manner discussed above with other contact probe assemblies. For example, a portion of another contact probe assembly 456 is shown in FIG. 13. The assembly 456 is substantially similar to probe assembly 409 except that a plurality of traces pads 457 are arranged on body 413 in a predetermined pattern instead of contact probes 411. Each pad 457, one of which is shown in FIG. 13, is formed on an electrical trace 458 disposed on surface 414 of the body. The traces 458 are made from any suitable material such as copper, silver, platinum, palladium, conductive carbon or platinum-laden polymers and other conductive inks such as metalized inks and blends of conductive materials and polymers such as conductive expoxies and conductive adhesives formed on surface 414. These materials can be so disposed on surface 414 by vapor deposition, screen or other printing, other traditional flex circuit methods or any other suitable means. Trace pads 457 can be made from any suitable material such as gold and/or the materials listed above for traces 458 and be formed on the end of the respective trace by any of the methods discussed above with respect to the traces 458. The bulbous contact portions 444b of microstructure device 406 depend from bottom surface 423 so as to facilitate electrical contact between the contact portions 444b and pads 457.

Figure 14:
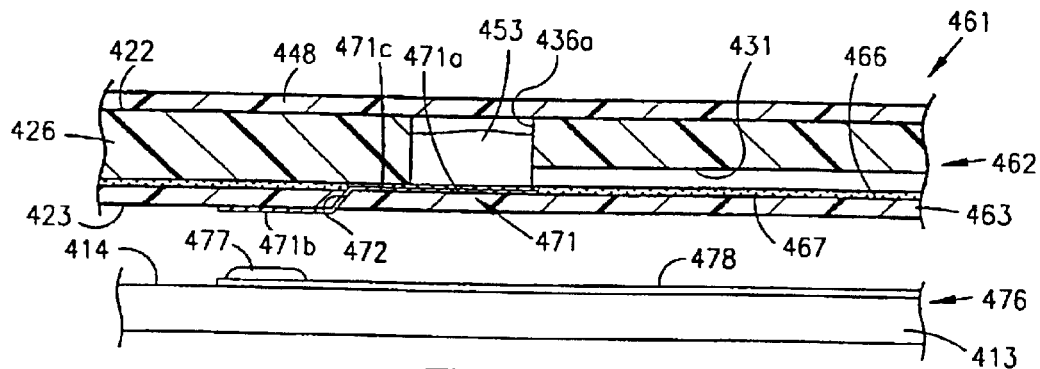
FIG. 14 is a cross-sectional view similar to FIG. 13 of another embodiment of a laminate microstructure device of the present invention and another embodiment of a contact probe assembly for use therewith.

In another embodiment, a microstructure device 461 substantially similar to the microstructure device 406 and for use with contact probe assembly 409 is shown in FIG. 14. Like reference numerals have been used to describe like components of microstructure devices 406 and 461. A laminate structure 462 substantially similar to laminate structure 421 is included within microstructure device 461. A second layer or lamina 463 is included in laminate structure 462 and has a first or upper planar surface 466 and a second planar surface in the form of bottom surface 423 of the laminate structure 462. Although the second lamina 463 is shown as being secured to first lamina 426 by an adhesive layer 467, it should be appreciated that surfaces 427 and 466 can be heat bonded or sealed together by any other suitable means. Microstructure device 461 is shown with a cover lamina 448, but it should be appreciated that the device 461 can be provided without a cover lamina 448 so that wells 436 are each accessible from the top surface or exterior of microstructure device 461.

A plurality of electrical means 471 are at least partially carried by second lamina 463. The electrical means 471 are preferably equal in number to the number of wells 436 provided in laminate structure 462 such that each of the wells 436 has a corresponding electrical means 471. Each of such electrical means 471 includes an electrode portion 471a which can communicate with the fluid supplied to the well 436 and a contact or pad portion 471b spaced-apart from electrode portion 471a and not in fluidic contact with any such fluid. Electrical means 471 each include a trace portion or trace 471c which electrically connects the respective electrode 471a to the contact portions 471b. As can be seen from FIG. 14, contact portion 471 is disposed adjacent and more specifically formed on bottom surface 423. Electrical trace 471c extends from the contact portion through a passage 472 extending transversely and more specifically diagonally between surfaces 466 and 423 of the second lamina 463 and has a further portion disposed on the upper surface 466 underlying electrode portion 471a. Second lamina 463 can be made from any suitable flex circuitry material such as acrylic, polyimide or PET. Contact portions 471b and portions of trace 471c can be formed from any suitable material such as copper, silver, platinum, palladium, conductive carbon or platinum-laden polymers and other conductive inks such as metalized inks and blends of conductive materials and polymers such as conductive expoxies and conductive adhesives formed on the aforementioned surfaces of second lamina 463. These materials can be so disposed on such surfaces of the second lamina by vapor deposition, screen or other printing, other traditional flex circuit methods or any other suitable means. Electrode portions 471a can be formed from any suitable material such as gold and/or the materials listed above for contact portions 471b and traces 471c and be formed on trace 471c by any suitable means such as those described above with respect to contact portions 471b and traces 471c. Each of the electrode portions 471a is shown as forming at least a portion of the bottom surface of the respective well 436. Alternatively, the electrode portions 471a can form the entire bottom surface of the well 436 or merely make fluidic contact with the well from a side wall or otherwise. Contact portions 471b are accessible from the exterior or bottom surface 423 of laminate structure 461 and microstructure device 461 and are each preferably spaced-apart from the centerline of the respective well 436. The contact portions 471b are arranged on the underside of microstructure device 461 in a pattern corresponding to the pattern of contact probes 411 on support structure 412.

Microstructure device 461 can be operated with contact probes 411 in substantially the same manner as described above with respect to microstructure device 406. Rounded ends 411a of the contact probes 411 can simultaneously engage the contact portions 471b for providing the desired electrical potential to the fluid in each of wells 436.

Microstructure device 461 can also be used in the manner discussed above with other contact probe assemblies. For example, a portion of another contact probe assembly 476 is shown in FIG. 14. The assembly 476 is substantially similar to probe assembly 409 except that a plurality of traces pads 477 are arranged on body 413 in a predetermined pattern instead of contact probes 411. Each pad 477, one of which is shown in FIG. 14, is formed on an lectrical trace 478 disposed on surface 414 of the body. The traces 478 are made from any suitable material such as those described above with respect to traces 457 of contact probe assembly 456 and are disposed on surface 414 by any suitable method such as those discussed above with respect to traces 457. Trace pads 477 can be made from any suitable material such as those described above with respect to electrical means 444. The bulbous trace pads 477 extend upwardly from surface 414 and traces 478 of contact probe assembly 476 so as to facilitate electrical contact between the contact portions 471b and trace pads 477.

Figure 15:
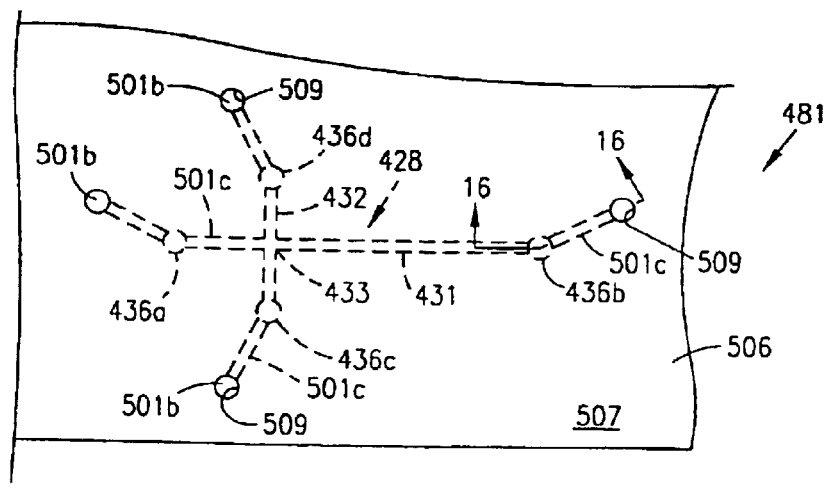
FIG. 15 is a plan view of a further embodiment of a laminate microstructure device of the present invention.
Figure 16:
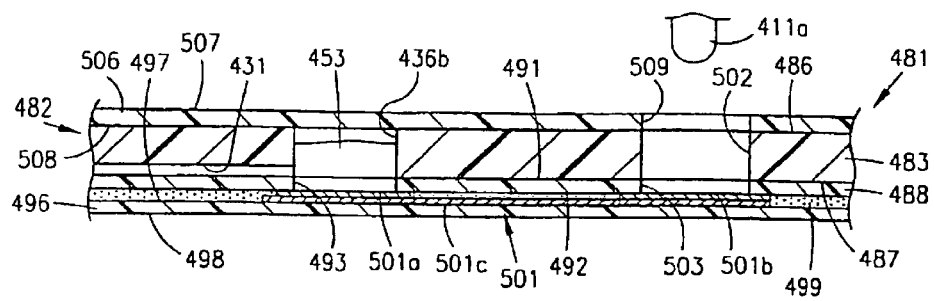
FIG. 16 is a cross-sectional view of the laminate microstructure device of FIG. 15 taken along the line 16—16 of FIG. 15.

A further embodiment of a microstructure device of the present invention is shown in FIGS. 15 and 16. Microstructure device 481 therein is substantially similar to microstructure devices 406 and 461 and is for use with contact probe assembly 409. Like reference numerals have been used to describe like components of devices 406, 461 and 481. A laminate structure 482 substantially similar to laminate structure 421 is provided in microstructure device 481. Laminate structure 482 includes a first layer or lamina 483 which is substantially similar to first lamina 426 and has first and second planar surfaces 486 and 487 extending in parallel directions. At least one and preferably a plurality of microstructures 428 are provided in laminate structure 482. One of microstructures 428 is shown in FIG. 15 and a portion of such microstructure 428 is shown in FIG. 16. The microstructures 428 are formed in laminate structure 482 in the same manner as they are formed in laminate structure 421. Specifically, each of the microstructures 428 is formed in first lamina 483 and opens onto second or lower surface 487 of the lamina 483. A plurality of wells 436 extend between surfaces 486 and 487 in fluid communication with the microstructure 428 and are each accessible from first or top surface 486 of laminate structure 482.

Laminate structure 482 includes an optional second layer or lamina 488 made from plastic or any other suitable material. Thin film or lamina 488 has a first or upper planar surface 491 and a second or lower planar surface 492 parallel to the upper surface 491. The upper surface 491 is secured to the lower' surface 487 of first lamina by diffusion bonding or any other suitable method. A bore 493 having a diameter substantially equal to the diameter of the well-forming bore in first lamina 483 extends between surfaces 491 and 492 for forming a part of well 436b. The combined thicknesses of laminae 483 and 488 determine the depth of wells 436. If a thin layer film is used for second lamina 488, the thickness of first lamina 483 can be increased to provide the desired depth to wells 436.

A third layer or lamina 496 is included in laminate structure 482. The third lamina 496 is substantially similar to second lamina 463 and has a first or upper planar surface 497 and a second or lower planar surface 498. Upper surface 497 of the third lamina 496 is secured to lower surface 492 of second lamina 488 by an adhesive layer 499 or any other suitable means. Upper surface 486 of the first lamina and lower surface 498 of the third lamina 496 form the top and bottom surfaces of laminate structure 482.

A plurality of electrical means 501 are at least partially carried by third lamina 496 for each microstructure 428 such that each of the wells 436 has a corresponding electrical means 501. More specifically, each electrical means 501 is disposed on upper surface 497 of the third lamina 496. Each such electrical means 501 has an electrode portion 501a, a pad or contact portion 501b and a trace portion or trace 501c. The electrical trace 501c is made from any suitable material such as any of the materials discussed above with respect to contact portions 471b and traces 471c and is disposed on upper surface 497 by any suitable means such as any of those described above with respect to contact portions 471b and traces 471c. The trace 501c has a first end portion underlying the respective well 436 and a second spaced-apart end portion underlying an access bore 502 extending between upper and lower surfaces 486 and 487 of the first lamina 483 and an access bore 503 extending between upper and lower surfaces 491 and 492 of second lamina 488. Electrode portion 501a consists of a layer of material disposed on the first end portion of trace 501c underlying well 436. Electrode portion 501a is shown in FIG. 16 as forming at least a portion of the lower surface of the well 436. Contact portion 501b consists of a layer of material disposed on the opposite second end portion of trace 501c and serves as the lower surface of access bores 502 and 503. Adhesive layer 499 extends around the base of bore 493 and over the portion of trace 501c between electrode portion 501a and contact portion 501c to provide a fluid seal at the bottom of the well 436. The electrode portion 501a and the contract portion 501b can each be made from any suitable material such as any of the materials discussed above with respect to electrode portions 471a and can be formed by any suitable means such as any of those described above with respect to contact portions 471b and traces 471c. Contact portions 501b are arranged on the bottom surface 498 of laminate structure 482 in a pattern corresponding to the pattern of contact probes 411 on support structure 412 and are accessible from such bottom surface 498.

Microstructure device 481 can optionally include a fourth layer or lamina 506 substantially similar to cover lamina 448 and having a first or upper surface 507 and a second or lower surface 508 heat bonded or otherwise suitably secured to upper surface 486 of the first lamina 483. Cover lamina 506 overlies each of wells 436 so as to sealably secure the fluid 453 within the well. An opening 509 is provided in cover lamina 406 in registration with access bores 502 and 503 for permitting contact probes 411 to engage contact portions 501b.

Microstructure device 481 can be operated in substantially the same manner as described above except that contact probes are disposed above the device 481. In this regard, contact probes 411 are positioned above microstructure device 481 such that rounded ends 411a of the contact probes 411 face downwardly toward openings 509 and contact portions 501b. When it is desired to transport fluids within microstructures 428, the microstructure device 481 and contact probes 411 are moved relative to each other such that rounded ends 411a enter openings 509 and electrically engage contact portions 501b.

The engagement of contact probes 411 with the top of microstructure device 481 allow less obscured access to the bottom of device 481 for purpose of optical detection and/or temperature control. Second lamina 488 provides an opposing surface 491 to the microstructures 428 formed in the first lamina which is not an adhesive. The inclusion of the second lamina 488 facilitates forming microstructures 428 from walls that are all of the same material, which can be advantageous in certain processes of device 481. In addition, the absence of fluid contact with the adhesive permits a broader selection of adhesives to be considered for adhesive layer 499.

Figure 17:
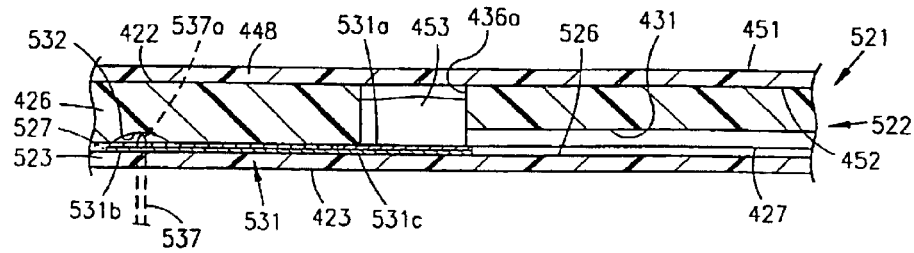
FIG. 17 is a cross-sectional view similar to FIG. 13 of yet another embodiment of a laminate microstructure device of the present invention and an contact probe for use therewith.

An embodiment of another microstructure device is shown in FIG. 17 where a portion of microstructure device 521 is depicted. The microstructure device 521 is substantially similar to microstructure device 406 and like reference numerals have been used to describe like components of devices 406 and 521. A laminate structure 522 substantially similar to laminate structure 421 is provided. A first lamina 426 having a plurality of microstructures 428 formed therein is included in the laminate structure 522. For simplicity, a portion of only a single microstructure 428 and one of the plurality of wells 436, specifically first well 436a, is shown in FIG. 17. A second layer or lamina 523 made from any suitable flex circuit material such as acrylic, polyimide or PET is included within laminate structure 522 and has a first or upper planar surface 526 and a second or lower planar surface in the form of bottom surface 423 of the laminate structure 522. Although the second lamina 523 is shown as being secured to first lamina 426 by an adhesive layer 527, it should be appreciated that surfaces 427 and 528 can be heat bonded or sealed together by any other suitable means. Microstructure device 521 is shown with a cover lamina 448, but it should be appreciated that the device 521 can be provided without a cover lamina so that wells 436 are each accessible from the top surface or exterior of microstructure device 521.

A plurality of electrical means 531 for each microstructure 428 are at least partially carried by second lamina 523 such that each of the wells 436 has a corresponding electrical means 531. More specifically, each electrical means 531 is disposed on upper surface 526 of the second lamina 523. Each such electrical means 531 has an electrode portion 531a, a pad of contact portion 531b and a trace portion or trace 531c. Trace 531c is made from any suitable material such as any of the materials discussed above with respect to contact portions 471b and traces 471c and is disposed on upper surface 526 by any suitable means such as any of those described above with respect to contact portions 471b and traces 471c. The trace 531c has a first end portion underlying the respective well 436 and a spaced-apart second end portion underlying a recess or cavity 532 formed in first lamina 426 and opening onto lower surface 427 thereof. Electrode portion 531a consists of a layer of material deposited on the first end portion of trace 531c underlying well 436 and is shown in FIG. 17 as forming at least a portion of the lower surface of well 436. Contact portion 531b consists of a layer of material disposed on the second end portion of trace 531c and preferably extends across the entire opening of recess 532 in lower surface 427. The electrode portion 531a and the contract portion 531b can each be made from any suitable material such as any of the materials discussed above with respect to electrode portions 471a and can be formed by any suitable means such as any of those described above with respect to contact portions 471b and traces 471c.

Microstructure device 521 is for use with a contact probe assembly (not shown) having piercing contact probes 537 and otherwise substantially similar to contact probe assembly 409. Contact probes 537 are substantially similar to contact probes 411 except that the probes 537 are capable of piercing the second lamina 523 and electrical means 531. Piercing contact probes 537 can have sharpened tips 537a. A portion of one contact probe 537 is shown in dashed lines in FIG. 17. Like contact probes 411, the probes 537 are arranged on support structure 412 in a predetermined pattern.

The second lamina 523 has a thickness and hardness which permits sharpened tips 537a of the contact probes 537 to penetrate the second lamina 523. Contact portions 531b and the portion of traces 531c thereunder are also of a thickness which permits penetration by sharpened tips 537a. Contact portions 531b are arranged on microstructure device 521 in a pattern corresponding to the pattern of contact probes 537. In a preferred embodiment, the number of contact probes 537 is at least equal to the number of contact portions 531b.

Microstructure device 521 can be operated and used in a manner described above. When it is desired to dectrokinetically transport the fluids within wells 436 of the microstructures 428 in the device 521, the operator causes relative movement between the structure device 521 and the contact probe assembly so that sharpened tips 537a of the contact probes 537 penetrate second lamina 523 and contact portions 531b and thus make electrical contact with electrical means 531. Thereafter, desired voltage potentials can be applied to the fluids in wells 436. The placement of puncturable contact portion 531b internally of microstructure device 521 eliminates exposed contact portions, which can be damaged from handling. The puncturable lamina 523 eliminates the need of access bores through other layers of laminate structure 522, which can add cost to the device 521.

Figure 19:
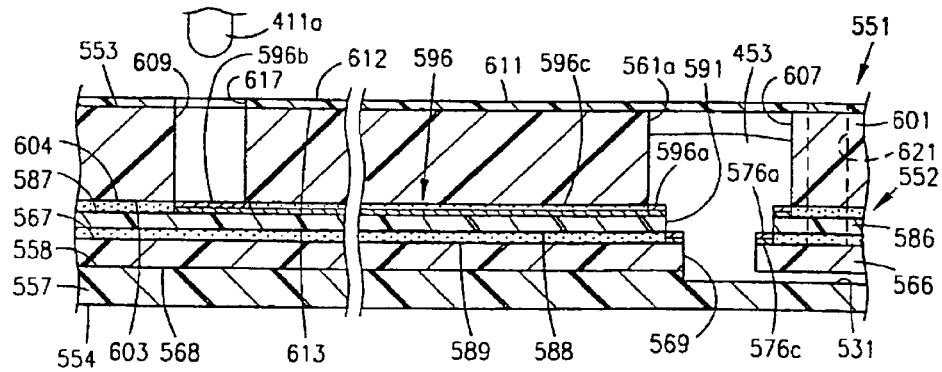
FIG. 19 is a cross-sectional view of the laminate microstructure of FIG. 18 taken along the line of 19—19 of FIG. 18.
Figure 18:
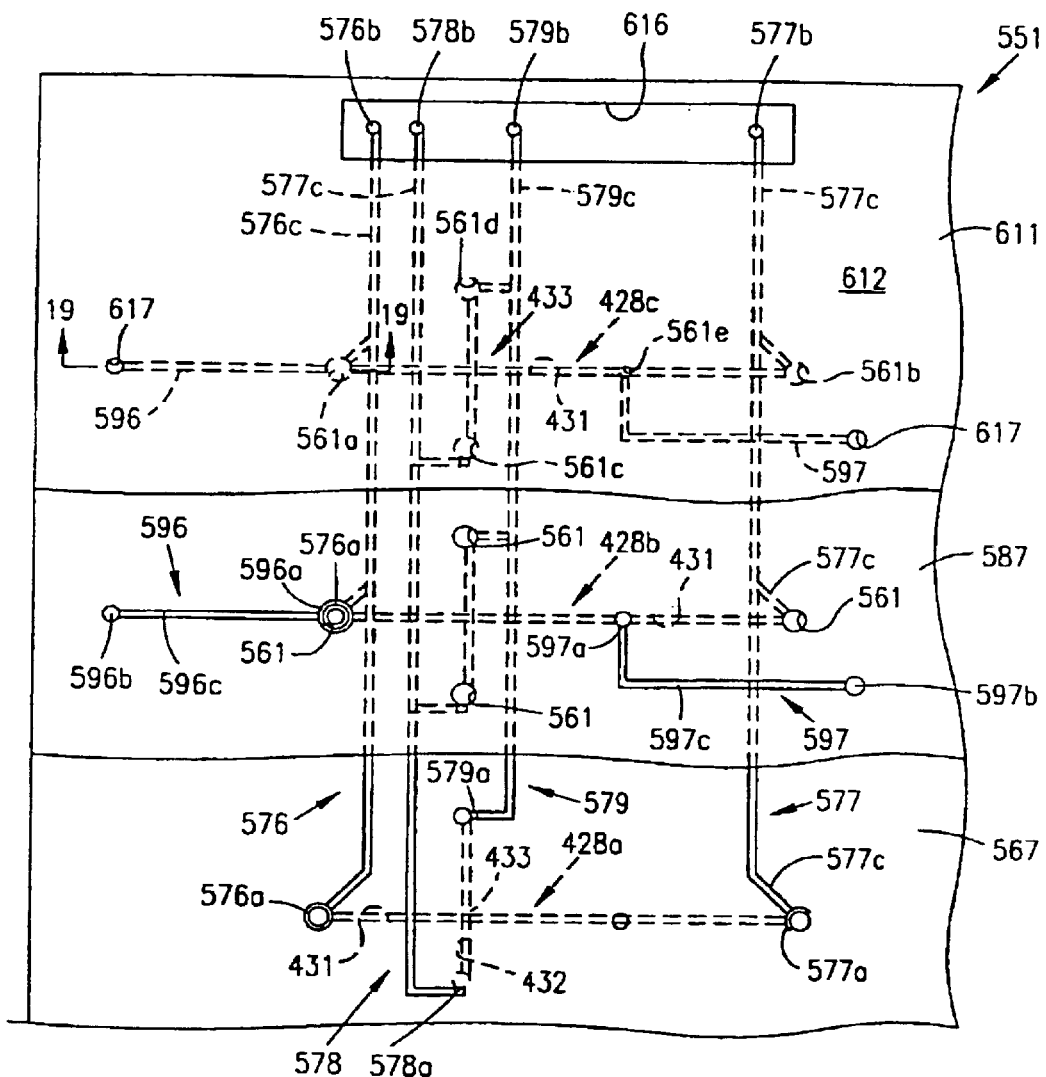
FIG. 18 is a top plan view, partially cut away, of another embodiment of a laminate microstructure device of the present invention.

In another embodiment of the invention, microstructure device 551 for use with contact probe assembly 409 is shown in FIGS. 18 and 19. Microstructure and device 551 is preferably a card-like device, but can also be an elongate flexible device suitable for storage on a reel. As such, microstructure device 551 can have a size and shape similar to microstructure device 406. The device 551 includes a laminate structure 552 having a first or top planar surface 553 and a second or bottom planar surface 554 spaced apart from the top planar surface 553. The surfaces 553 and 554 form a portion of the exterior of the laminate structure. A first layer or lamina 557 is included within laminate structure 552 and is made from any suitable non-conductive materials such as plastic. The first lamina 557 can be relatively rigid or flexible depending on the particular use and configuration of the microstructure device 551. Alternatively, other layers in laminate structure 552 can be relatively rigid, in addition to or instead of a rigid lamina 557, if a rigid microstructure device 551 is desired. First lamina 557 has a first planar surface in the form of first or upper surface 558 and a second planar surface 554 spaced-apart from the upper surface 558.

The laminate structure 552 is provided with at least one microstructure 428 and preferably a plurality of microstructures 428 formed therein and extending in a direction parallel to the parallel surfaces 558 and 554 of the first lamina 557. A plurality of three microstructures 428, namely first microstructure 428a, second microstructure 428b and third microstructure 428c, are shown in FIG. 18. A portion of third microstructure 428c is shown in FIG. 19. Each of the microstructures 428 is formed in first lamina 557 and opens through one of the planar surfaces 554, 558 of the first lamina. In the embodiment shown, the microstructures 428 open onto upper surface 558 of the first lamina 557. Laminate structure 552 has at least one and as shown a plurality of holes or wells 561 substantially similar to wells 436.

Specifically, first and second wells 561a and 561b are provided at the first and second ends of first microchannel 431 and third and fourth wells 561c and 561d are provided at the first and second ends of second microchannel 432. It should be appreciated that wells 561 can be provided at other locations within microstructure 428. For example, a fifth well 561e is provided in an intermediate portion of first microchannel 431 between wells 561a and 561b.

Laminate structure 552 has a second layer or lamina 566 made from any suitable non-conductive material such as plastic overlying first lamina 551. More specifically, second lamina 556 can be made from any suitable flex circuit material such as acrylic, polyimide or PET. The second lamina 556 has a first or upper planar surface 567 and a second or lower planar surface 568 which is spaced-apart from and parallel to upper surface 567. A portion of microstructure device 551 is cut away in FIG. 18 to expose a portion of upper surface 567. Second lamina 566 is secured to first lamina 557 by any suitable means such as heat bonding together surfaces 558 and 568. A plurality of bores 569 extend through surfaces 567 and 568 for forming the first or lower segment of respective wells 561.

A plurality of electrical means similar to the electrical means described above are at least partially carried by second lamina 566. More specifically, such electrical means are carried by upper surface 567 of the second lamina 566 and thus extend in a single plane. A plurality of four electrical means 576–579 are shown in FIGS. 18–19. First electrical means 576 includes an electrode portion 576a, a pad or contact portion 576b and a trace portion or trace 576c. Electrical trace 576c is made from any suitable material such as any of the materials discussed above for contact portions 471b and traces 471c disposed on surface 567 by any suitable means such as any of those described above with respect to contact portions 471b and traces 471c. The trace 576c has a plurality of first end portions adjacent the respective first wells 561a of first microstructure 428a, second microstructure 428b and third microstructure 428c. The first end portion of trace 576c in the vicinity of first well 561a for third microstructure 428c is shown in cross-section in FIG. 19. Such trace end portion is annular in shape, although any suitable shape can be provided. An electrode portion 576a of any suitable shape is disposed on the first end portion of each trace 576c. The electrode portion 576a for first well 561a of third microstructure 428c is annular in shape and extends around the respective bore 569 in the second lamina 566. More specifically, such annular electrode portion 576a is concentrically disposed about the well 561a. An opening is provided in the center of each annular electrode portion 576a for forming part of the respective well 561a. A contact portion 576b is disposed on the second end portion of each trace 576c. The electrode portion 576a and the contract portion 576b can each be made from any suitable material such as any of the materials discussed above with respect to electrode portions 471a and can be formed by any suitable means such as any of those described above with respect to contact portions 471b and traces 471c.

Second electrical means 577 has an electrode portion 577a, a pad or contact portion 577b and a trace portion or trace 577c substantially similar in construction and material to the corresponding portions of first electrical means 576. The electrical trace 577c has a plurality of first end portions adjacent each of second wells 561b and a second end portion in the vicinity of the contact portion 576b of the first electrical means 576. An electrode portion 577a of any suitable shape is disposed on the first end portion of each trace 577c. As can be seen from FIG. 18, the electrode portion 577a for first microstructure 428a is arcuate or horseshoe in shape. Specifically, electrode portions 577a and the portion of traces 577c thereunder each subtend an angle of approximately 90° about the centerline of the respective well 561b. Contact portion 577b is disposed on the second end portion of trace 577c adjacent contact portion 576b.

Third electrical means 578 has an electrode portion 578a, a pad or contact portion 578b and a trace portion or trace 578c substantially similar to the corresponding portions of second electrical means 577. Electrical trace 578c has a first end portion adjacent each of third wells 561c and a second end portion adjacent contact portions 576b and 577b. An electrode portion 578a is deposited on the first end of each trace 578c adjacent the respective well 561c and engages only a portion of the well 561c. Each electrode portion 578a and the portion of the trace 578c thereunder subtend an angle of less than approximately 30° with respect to the centerline of the respective well 561c and are disposed in the well diametrically opposite the entrance of microchannel 432 in the well. Contact portion 578b is deposited on the second end portion of trace 578c in the vicinity of contact portions 576b and 577b. Fourth electrical means 579 has an electrode portion 579a, a pad or contact portion 579b and a trace portion or trace 579c, each formed of the materials of the corresponding portions of the first electrical means 576 and deposited onto upper surface 567 in the same manner as first electrical means 576. The electrical trace 579c has a first end portion adjacent each of fourth wells 561d and a second end portion in the vicinity of contact portions 576b, 577 and 578b. An electrode portion 579a is deposited on each first end portion of trace 579c adjacent the respective well 561d and, as shown in FIG. 18, has a shape similar to that of electrode portion 578a.

A third layer or lamina 586 is included within laminate structure 552 and overlies second lamina 566. The third lamina 586 is similar in construction, size and composition to second lamina 566 and has a first or upper planar surface 587 and a second or lower planar surface 588 extending parallel to upper surface 587. A portion of microstructure device 551 is cut away in FIG. 18 to expose a portion of upper surface 587. Lower surface 588 of the third lamina 586 is secured to upper surface 567 of the second lamina 566 by an adhesion layer 589, although laminae 566 and 586 can be secured together by any other suitable means such as heat bonding. A plurality of bores 591 extend between upper and lower surfaces 587 and 588 forming the second or intermediate segments of each of the wells 561 of microstructure device 551. Bores 591 each have an inner diameter greater than the inner diameter of bores 569 in the second lamina 566 so that the intermediate segment of wells 561 is larger in diameter than the lower segment of the wells formed by bores 569. The inner diameter of bores 591 is sufficiently large so that electrode portions 576a, 577a, 578 and 579a formed on the second lamina 566 are exposed to the fluid 453 within the wells 561. An opening, shown but not identified in FIG. 18, is provided through surfaces 587 and 588 for permitting access to contact portions 576b, 577b, 578b and 579b through the third lamina 586.

A plurality of electrical means substantially similar to the electrical means on second lamina 566 are at least partially carried by third lamina 586. Specifically, a plurality of fifth electrical means 596 and a plurality of sixth electrical means 597 are carried on upper surface 587 for each of the microstructures 428 formed by laminate structure 552. For simplicity, fifth and sixth electrical means 596 and 597 are shown only with respect to second microstructure 428b and third microstructure 428c in FIGS. 18 and 19. The fifth and sixth electrical means 596 and 597 are substantially similar in construction and materials to electrical means 576–579 described above. Each of the fifth electrical means 596 has an electrode portion 596a, a pad or contact portion 596b and a trace portion or 596c. Each electrical trace 596c has a first end portion adjacent the respective first well 561a and a second end portion spaced-apart from the respective well 561a. The first end portion of each trace 596c is annular in shape, although any suitable shape can be provided, and extends around the first well 561a. An electrode portion 596a which is shown as being annular in shape is deposited on top of the first end portion of each trace 596c. The first end portion of each trace 596c and each electrode portion 596a has an opening in the center thereof forming a part of the respective first well 561a. A contact portion 596b is deposited atop the second end portion of each trace 596c. Each sixth electrical means 597 has an electrode portion 597a, a pad or contact portion 597b and a trace portion or trace 597c. Each electrical trace 597c has a first end portion adjacent the respective fifth well 561e and a second end portion spaced-apart from the well 561e. An electrode portion 597a is disposed atop the first end portion of each trace 597c and is adapted to contact the fluid within the fifth well 561e. In this regard, each electrode portion 597a is substantially similar to electrode portions 577a and 578a described above. A contact portion 597b is deposited atop the second end portion of each electrical trace 597c.

Laminate structure 552 has a fourth layer or lamina 601 made from any suitable material such as plastic which overlies third lamina 586. Lamina 601 can be relatively rigid if a rigid microstructure device 551 is desired. Fourth lamina 601 has a first or upper planar surface consisting of top surface 553 of the laminate structure 552 and a second or lower planar surface 603 extending parallel to the upper surface 553. Lower surface 603 is adhered to upper surface 587 of third lamina 586 by an adhesion layer 604 or any other suitable means. A plurality of bores 607 extend between surfaces 553 and 603 for forming a third or upper segment of each of the wells 561 in microstructure device 551. The bores 607 each have an inner diameter greater than the inner diameter of bores 591 so that the upper segment of the wells 561 is larger in diameter than the lower and intermediate segments of the wells. The inner diameter of bores 607 is sufficiently large such that electrode portions 596a and 597a are exposed so as to contact the fluid within the wells. An additional opening, shown but not identified in FIG. 18, is provided between surfaces 553 and 603 to permit access to contact portions 576b, 577b, 578b and 579b through the fourth lamina 601. A further plurality of bores 609 extend between surfaces 553 and 603 in registration with contact portions 596b and 597b to permit access to the fifth and sixth electrical means 596 and 597.

The aggregate thicknesses of laminae 566, 586 and 601 determine the depth of wells 561. Second and third laminae 566 and 586 can each have a thickness ranging from 40 to 250 microns. Fourth lamina 601 can have a thickness ranging from 250 microns to one millimeter. As can be seen, laminae 566 and 586 can be films backing a thick fourth lamina 601.

A fifth layer or lamina 611 is included in microstructure 551 for serving as a cover layer. Cover lamina 611 is substantially similar to cover lamina 448 described above and has a first or upper planar surface 612 and a second or lower planar surface 613 extending in a direction parallel to upper surface 612. Lower surface 613 is secured to upper surface 553 of the fourth lamina 601 by heat bonding or any other suitable means. An opening 616 extends through surfaces 612 and 613 to permit access to contact portions 576b, 577b, 578b and 579b. In addition, a plurality of bores 617 extend between surfaces 612 and 613 in registration with bores 609 to permit access to contact portions 596b and 597b. The contact portions of electrical means 576–579 and 596–597 and wells 561 are accessible from top surface 553 of the laminate structure 552. It should be appreciated that microstructure device 5551 can be provided without a cover lamina 611 and be within the scope of the present invention.

One or more optional detection bores 621 can extend through any or all of cover lamina 611, third and fourth laminae 586 and 601 and adhesive layers 589 and 604 for each microstructure 428 to facilitate optical detection by a detector (not shown) of fluid within microstructures 428. One such bore 621 is shown in dashed lines in FIG. 19. Such bores minimize undesirable fluorescence which can be provided by such layers and adhesives.

Although microstructure device 551 is shown and described as having first and second laminae or flex circuit layers 566 and 586, electrical means 576–579 can be formed on upper surface 558 of first lamina 557 by any suitable manner, such as any of the methods described above, so as to eliminate second lamina 566. Alternatively, electrical means 576–579 can be formed on lower surface 588 of third lamina 496, the invention being broad enough to cover overlapping electrical means of the type described above separated by an insulating or nonconductive layer.

In operation and use, microstructure device 551 can be used with electrode assembly 409 for any of the processes and methods described above. In this regard, rounded ends 411a of the contact probes 411 are extended through top surface 553 of the laminate structure to simultaneously engage contact portions 576b, 577b, 578b, 579b, 596b and 597b. Appropriate voltage potentials are then applied to the fluids 453 within wells 561 to electrokinetically move fluids with the plurality of microstructures 423 provided in microstructure device 551.

During such operation, each of traces 576c, 577c, 578c and 579c permit a single contact probe 411 to be utilized for providing a voltage potential to the respective plurality of wells 561 electrically coupled thereto. Fifth well 561e and sixth electrical means 577 can be utilized to assist the movement of fluid within microstructure 551 between the first and second end portions of first microchannel 431. The location of the electrode portions in the well at a point farthest from the opening of the microstructure 428 in the well, such as electrode portions 578a which is diametrically opposite the opening of the respective microstructures, enhances electrokinetic movement of fluids into and from the well by maximizing the amount of fluid in the relevant microchannel which is between the operative electrode portions. Arcuate or horseshoe-shaped electrode portions, such as electrode portions 577a, can be similarly disposed opposite the microstructure opening in the well to focus the electrical potential towards the microchannel of the microstructure.

The wells 561 in microstructure device 551 are formed in layers other than the layer(s) forming microstructures 428. It has been found that such wells 561 can be more easily manufactured, for example in a punching operation, when not present in the layer forming microstructure or microstructures 428. The depth of wells 561 so formed is determined by the thickness and number of such other layers in laminate structure 552.

The inclusion of two flex circuit layers in laminate structure 552, that is second and third lamina 566 and 586, permit complex and/or dense patterns of electrodes and electrical traces to be provided in microstructure device 551. For example, traces on one of such flex circuits can extend over or under traces on the other such flex circuit, the traces being electrically insulated from each other by one of the lamina of the laminate structure 552. The insulating separation layer minimizes cross talk between the crossing traces. The electrodes, electrical traces and contact pads can also cross over or under the microchannels or other portions of microstructures 428. Such multi-layered electrical patterns permit a greater number of microstructures 428 and/or more elaborate microstructure designs to be provided on a given surface area of microstructure device 551. The first and second flex circuits also permit more than one contact probe to supply a voltage potential to a particular well 561 or other portion or the microstructures 428. For example, a voltage potential can be applied to the fluid 453 in first well 561 *a* of microstructure device 551 by either first electrical means 576 or fifth electrical means 596. The multiple layers of flex circuits can also facilitate placement of the contact portions along one side of the device, such as shown in FIG. 18 with contact portions 576*b*, 577*b*, 578*b* and 579*b*.

It should be appreciated that the illustrated configurations of electrodes and electrical traces on second and third lamina 566 and 586 can be combined in a multitude of ways to provide a variety of microstructure devices 551. In this regard, the electrode portions can be sized as desired and can be provided in wells or other portions of microstructures 428. One or more electrode portions can be provided for each well so as to permit one or more voltage potentials to be alternatively or otherwise applied to the well. A single trace can be used to transmit a voltage potential to a single well or to a plurality of wells. More than two flex circuit layers can also be provided in other embodiments of the microstructure device of the present invention.

A microstructure device substantially similar to device 551 can be provided without electrical means of type described above integrated therein. For example, flex circuit layers 566 and 586 can be eliminated from device 551 to provide a laminate with microstructures 428 and wells 561, but not electrical means 576–579 and 596–597.

The invention herein can be broadly claimed as a microstructure device comprising a laminate structure having a first lamina being provided with at least one microstructure extending in a direction parallel to the first and second parallel surfaces of the first lamina. The laminate structure is provided with a plurality of spaced-apart bores in the first lamina or a second lamina for forming at least a portion of a plurality of wells in fluid communication with the at least one microstructure. Electrical means of the type described above is carried by the laminate structure for each of the plurality of wells. Optionally, the first lamina is provided with an additional such microstructure and the laminate structure is provided with an additional plurality spaced-apart bores in one of its lamina for forming at least a portion of an additional plurality of wells in fluid communication with the additional microstructure. Optional additional electrical means can be carried by the laminate structure for each of the additional plurality of wells, the additional electrical means overlying the first-named electrical means and being electrically insulated from the first-named electrical means. An insulating layer of the lamina structure can optionally be disposed between the first-named and additional electrical means.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for microfluidic processing samples, the method comprising the steps of:
   providing a flexible elongate laminate having a plurality of microstructures arranged therein, the flexible elongate laminate comprising a first lamina having a first surface, a second lamina having a second surface, and a flexible circuit laminate adjacent to the first lamina, (i) wherein at least one of the first or second lamina has a plurality of openings so that whenever the first surface of the first lamina apposes the second surface of the second lamina each opening of the plurality of openings is in fluid communication with one of said plurality of microstructures, (ii) wherein the flexible circuit laminate comprises a plurality of electrodes, each electrode being in contact with an electroflow medium whenever the electroflow medium is suppled to said microstructures, and (iii) wherein each of said microstructures has a detection region;
   introducing a sample into each of said microstructures;
   conducting an assay on the sample in each of said microstructures to form one or more analytes in the electroflow medium; and
   electrophoretically separating the one or more analytes by creating a voltage differential between electrodes so that the one or more analytes are detected in the detection region in each of said microstructures.

2. The method of claim 1 wherein said step of introducing includes electrokinetically injecting said sample into each of said microstructures.

3. The method of claim 1 wherein said step of introducing includes electrokinetically injecting said sample into a reaction chamber of each of said microstructures.

4. The method of claim 3 wherein said assay in each of said microstructures is conducted in said reaction chamber to form said one or more analytes.

5. The method of claim 1 wherein said flexible elongate laminate is moved relative to a detector having a detection field so that said detection region of each of said microstructures is brought within such detection field and a signal produced by said one or more analytes in said detection region is detected or measured.

6. The method according to any of claims 1, 2, 3, 4, or 5 wherein said assay is selected from the group consisting of enzyme assays and receptor binding assays.

7. The method of claim 6 wherein said first lamina, said second lamina, and said flexible circuit laminate are plastic.

8. A microstructure device for detecting one or more analytes produced in a plurality of assays, the microstructure device comprising a flexible elongate laminate hating a plurality of microstructures arranged therein, the flexible elongate laminate comprising a first lamina having a first surface, a second lamina having a second surface, and a flexible circuit laminate adjacent to the first lamina, wherein at least one of the first or second lamina has a plurality of openings so that whenever the first surface of the first lamina apposes the second surface of the second lamina each opening of the plurality of openings is in fluid communication with one of said plurality of microstructures, and wherein the flexible circuit laminate comprises a plurality of electrodes, each electrode being in contact with an electroflow medium whenever the electroflow medium is supplied to said microstructures, each of said microstructures comprising:

a sample supply reservoir at an opening;

a sample drain reservoir connected to the sample supply reservoir by one or more microchannel segments;

an elution buffer reservoir;

an analyte waste reservoir; and a separation channel connecting the elution buffer reservoir and the analyte waste reservoir and intersecting and being in fluid communication with said one or more microchannel segments.

9. The microstructure device of claim 8 wherein said plurality of said microstructures comprises an array of microchannel structures.

10. The microstructure device of claim 9 wherein said microstructures of said array are arranged in a 12×8 orthogonal arrangement or in a 24×16 orthogonal arrangement.

11. The microstructure device of claim 9 wherein said first lamina, said second lamina, and said flexible circuit laminate are plastic.

12. A microstructure device for detecting one or more analytes produced in a plurality of assays, the microstructure device comprising a flexible elongate laminate having an array of microchannel structures arranged therein, the flexible elongate laminate comprising a first lamina having a first surface and a second lamina having a second surface, wherein at least one of the first or second lamina has a plurality of openings so that whenever the first surface of the first lamina apposes the second surface of the second lamina each opening of the plurality of openings is in fluid communication with one of said plurality of microstructures, each of said microstructures comprising:

a sample supply reservoir at an opening;

a sample drain reservoir connected to the sample supply reservoir by one or more microchannel segments;

an elution buffer reservoir;

an analyte waste reservoir;

a separation channel connecting the elution buffer reservoir and the analyte waste reservoir and intersecting and being in fluid communication with said one or more microchannel segments; and a plurality of electrodes connected to conductive traces to generate an electric field between the sample supply reservoir and the sample drain reservoir when an electroflow medium is present in the one or more microchannel segments and to generate an electrical field between the elution buffer revervoir and the analyte waste reservoir when an electroflow medium is present in the separation channel.

* * * * *